US011506874B2

(12) United States Patent
Banerjee et al.

(10) Patent No.: US 11,506,874 B2
(45) Date of Patent: Nov. 22, 2022

(54) OPTICAL IMAGING SYSTEMS AND FORMATION OF CO-ORIENTED AND CO-DIRECTIONAL IMAGES IN DIFFERENT FIELDS OF VIEW OF THE SAME

(71) Applicant: OMNISCIENT IMAGING INC., Tucson, AZ (US)

(72) Inventors: Bhaskar Banerjee, Tucson, AZ (US); Brian Scaramella, Tucson, AZ (US); Richard Pfisterer, Tucson, AZ (US); Scott Ellis, Tucson, AZ (US)

(73) Assignee: OMNISCIENT IMAGING, INC., Tucson, AZ (US)

( * ) Notice: Subject to any disclaimer, the term of this patent is extended or adjusted under 35 U.S.C. 154(b) by 255 days.

(21) Appl. No.: 17/087,934

(22) Filed: Nov. 3, 2020

(65) Prior Publication Data

US 2021/0278645 A1    Sep. 9, 2021

Related U.S. Application Data

(60) Provisional application No. 62/987,083, filed on Mar. 9, 2020.

(51) Int. Cl.
*G02B 17/08* (2006.01)
*H04N 5/225* (2006.01)
*G02B 13/18* (2006.01)
*A61B 1/00* (2006.01)

(52) U.S. Cl.
CPC ......... *G02B 17/0856* (2013.01); *G02B 13/18* (2013.01); *H04N 5/2253* (2013.01); *H04N 5/2254* (2013.01); *A61B 1/00181* (2013.01); *H04N 2005/2255* (2013.01)

(58) Field of Classification Search
CPC .. G02B 17/0856; G02B 13/18; H04N 5/2253; H04N 5/2254; H04N 2005/2255; A61B 1/00181
USPC .......................................................... 348/82
See application file for complete search history.

(56) References Cited

U.S. PATENT DOCUMENTS

| 7,801,584 | B2 | 9/2010 | Iddan | |
|---|---|---|---|---|
| 2016/0088204 | A1* | 3/2016 | Liang | A61B 1/012 348/68 |
| 2016/0338575 | A1* | 11/2016 | Honda | G02B 23/2423 |
| 2016/0345808 | A1* | 12/2016 | Inomata | A61B 1/00011 |

* cited by examiner

*Primary Examiner* — Joseph G Ustaris
*Assistant Examiner* — Matthew David Kim
(74) *Attorney, Agent, or Firm* — Quarles & Brady LLP; Yakov S. Sidorin

(57) ABSTRACT

Optical imaging systems configured to image object space in multiple fields-of-view (FOVs)—front and lateral FOVs—and form corresponding images that are co-oriented and co-directional regardless of mutual repositioning of the object and imaging systems. Images formed with such optical systems in which FFOV— and LFOV-image portions are co-directional. Co-directionality of formed images is achieved due to direct imaging with a system utilizing a specific involute reflective surface or as a result of radial spatial redistribution of irradiance of an initial image(s), formed with a system devoid of an involute reflective surface, while maintaining aspect ratios of dimensions of corresponding pixels of initial and transformed images. Methodology of transformation of images utilizing radial redistribution of image irradiance.

13 Claims, 22 Drawing Sheets

In Plane of Optical Detector

In Plane of Optical Detector

FIG. 18B
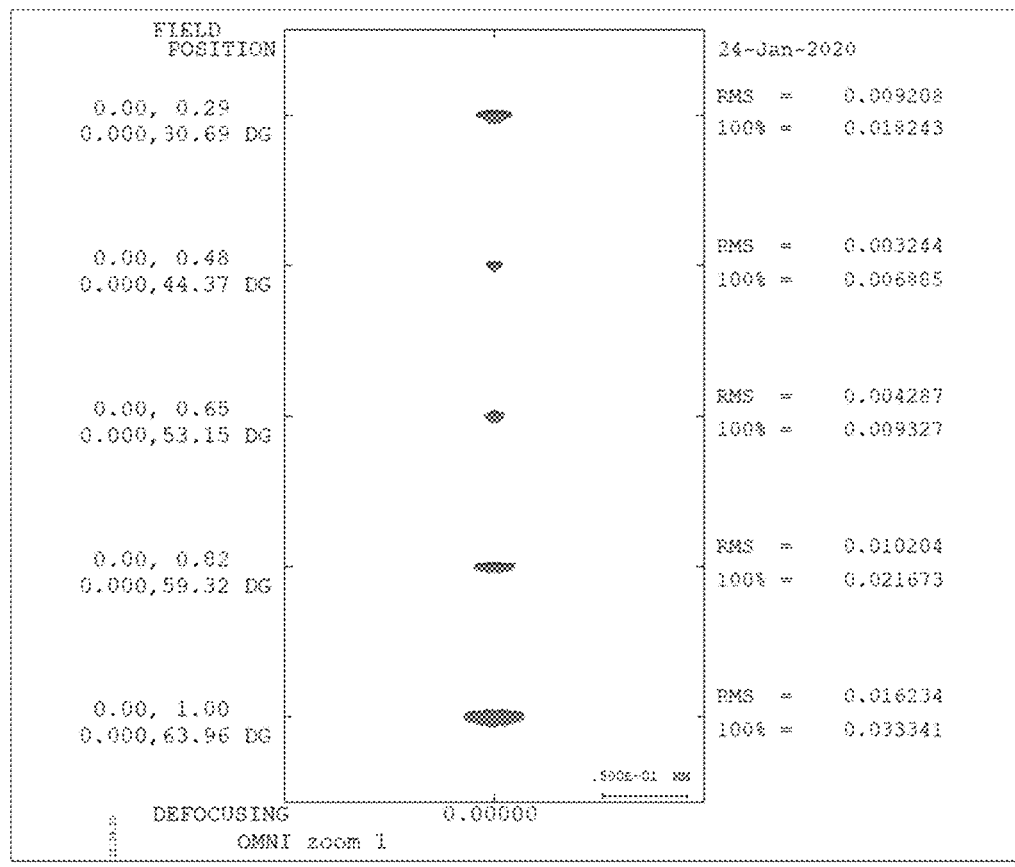
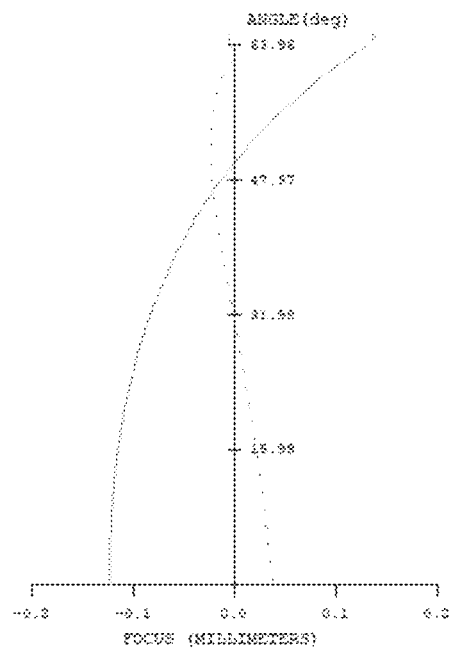
FIG. 18C

OPTICAL IMAGING SYSTEMS AND FORMATION OF CO-ORIENTED AND CO-DIRECTIONAL IMAGES IN DIFFERENT FIELDS OF VIEW OF THE SAME

CROSS-REFERENCE TO RELATED APPLICATIONS

This patent application claims priority from and benefit of the U.S. Provisional Patent Application No. 62/987,083 filed on Mar. 9, 2020. The disclosure of the above-identified provisional application is incorporated herein by reference.

TECHNICAL FIELD

This invention relates to specifically-structured multi-view optical imaging systems and methodologies directed to formation of optical images different portions of which remain co-oriented and co-directional regardless of mutual repositioning of such optical imaging systems and the object space.

RELATED ART

Imaging devices for viewing identified targets inside the human body have substantially evolved from the initial systems structured a la a simple telescope. The same holds true with respect to systems configured for the inspection of pipes and other practically-important cavities (such as aircraft turbines, complex machineries and tight spaces in buildings or bridges, for example). Whereas the ability to view forward (the forward-viewing) may be preferred for navigation through the ambient surroundings, when the surroundings include tubular structures the regions of interest and related important information are more often than not located sideways or even in a backward direction(s). The ability to procure lateral (or oblique or rear) views of the object space provides the advantage of allowing structures such as the inner walls of pipes or intestines (or areas behind objects or folds in the intestinal tract, to name just a few) to be viewed substantially simultaneously with one another and repetitively without having to change a position and/or orientation of the viewing system. Indeed, repositioning the optical system and turning backwards (as compared with the original orientation) can be difficult or even impractical to do in enclosed spaces with limited room for movement. Additionally, such required "repositioning and reorientation" understandably lengthens the time required for inspection of the target object space.

Many practical applications of imaging probes require repetitive imaging of regions located behind various obscurations. For instance, the intestinal tract, including the colon (while it can be accessed through a small opening) is not straight but highly convoluted in shape, dynamically mobile—that is, changing its shape as a function of time and biological processes occurring in the body—and has about a hundred folds that restrict the ability of the user to observe what is behind such folds. Although such views can be obtained by retro-flexing the tip of a forward-viewing scope, for example, the require operation often not physically implementable and does not provide a complete view behind the folds.

In another example, for the inspections of pipes, machinery, and aircraft turbines (all of which are the examples of fixed structures permitting only limited access), repetitive views in the backwards or sideways directions are very often required but can only be carried out by using a specific hardware attachment to the already existing optical system (such as a boroscope) that is designed to look backwards or sideways. Removing a borescope to attach a device for repetitive, non-forward views is time-consuming and impractical.

A skilled artisan is well aware that (even with all these practical problems alleviated to some degree by employing an optical imaging system capable of being reconfigured to "see" first forwards and then sideways of backwards, for example), the optical images of views acquired from different spatial directions upon continued repositioning of the optical system along a chosen axis inside the tubular structure (and while pointing such optical system in different spatial direction) not only remain spatially mismatching with one another, as is discussed below, but also often cannot be spatially stitched (and, at that, contain "dead", image-free zones separating different view and often shaped annularly).

SUMMARY

Embodiments of the present invention address the inability of conventionally-structured optical imaging systems having front field-of-view and a lateral field of view to form co-directional images of the portions of the object space covered by the front field of view and the lateral field of view of such systems. In particular:

Embodiments of the invention include a method for operating an optical system that has an optical axis, a front field of view (FFOV), and a lateral field of view (LFOV) to form an optical image in an image plane of the optical system. Such method includes at least the steps of (a) transmitting first light emanating from an object space through a first group of lens elements and a second group of lens elements to form a first portion of the optical image, the first portion including an axial point and having a first perimeter that circumscribes the optical axis; and (b) at least partially reflecting second light emanating from the object space with an optical reflector having reflective involute surface to form reflected light and transmitting the reflected light through a second group of lens elements to form a second portion of said optical image, the second portion dimensioned as a stripe or band having a second perimeter and located outside of the first perimeter. Here, the first portion of the optical image represents a first portion of the object space covered by the FFOV, the second portion of the optical image represents a second portion of the object space covered by the LFOV, a first object point of the object space is represented by a corresponding first image point at a first radial distance from the optical axis in the image plane; and wherein a first directionality of the first portion of the optical image and a second directionality of the second portion of the optical image are the same. The method may further include transmitting the first light through an aperture of the optical reflector that is disposed to spatially separate the first and second groups of lenses along the optical axis. Alternatively or in addition, the method may be configured such as to satisfy at least one of the following conditions: i) the step of transmitting the reflected light includes forming the second portion of the optical image without rotating the optical system about the optical axis; ii) the step of at least partially reflecting second light includes at least partially reflecting the second light with the optical reflector that is a stand-alone optical reflector a spatial profile of which, defined in a plane containing the optical axis, is not an analytic function of a viewing angle of the optical system; iii) the step of at least partially reflecting second light includes at least partially reflecting the second light with the optical reflector that is an optical reflector a spatial profile of which, considered in a plane containing the optical axis, is defined piecewise by polynomials as a function of a viewing angle of the optical system; and iv) the step of the at least partially reflecting second light includes at least partially reflecting the second light with the optical reflector defined by a reflective surface of a mangin mirror element. Moreover, in any of the above implementations the method may additionally include a step of mutually repositioning the optical system in a positive direction of the optical axis with respect to the object space to form an updated optical image (here, the first object point of the object space is represented by an updated first image point of the update optical image at a second radial distance from the optical axis in the image plane, and the second radial distance is larger than the first radial distance regardless of whether the first object point is viewed by the optical system in the FFOV or the LFOV).

Embodiments of the invention also include an optical imaging system having a front field of view (FFOV), a lateral field of view (LFOV). Such optical system contains a first optical subsystem and a second optical subsystem. The first optical subsystem includes a first optical detector, and a front lens (that faces a first portion of the object space covered by the FFOV and is dimensioned to form a first image of said first portion of the object space at the first optical detector). The second optical subsystem includes a second optical detector, and a rear lens (that faces a first portion of the object space covered by the LFOV and is dimensioned to form a second image of said second portion of the object space at the second optical detector). Here, the front and rear lenses are spatially separated from one another with the first and second optical detectors. The optical imaging system additionally includes a programmable electronic circuitry operably connected to the first and second optical detectors and is configured to form these first and second images having opposite directionalities. In addition, a first axis of the first optical subsystem and a second axis of the second optical subsystem may be inclined with respect to one another at a non-zero angle and/or the first and second lenses may be configured to be substantially identical. In any of the implementations of the optical imaging system, at least one of the first and second lenses may be a dioptric lens.

Moreover, embodiments of the invention include a method for transforming an image of the object space acquired with the use of an optical system in a lateral FOV (LFOV), the optical system having an optical axis and said lateral FOV (LFOV). Such method includes a) forming the image dimensioned as an annular stripe or band having inner and outer perimeters by collecting light from the LFOV through an edge surface of an element of the optical system; b) transforming spatial distribution of irradiance of such image to create a transformed image in which the irradiance is radially redistributed with respect to a circle of a chosen radius located between inner and outer perimeters of said portion of the image; and c) generating a report containing at least one of a first visually-perceivable representation of the image and a second visually-perceivable representation of the transformed image. In a specific case, the step of collecting light may include collecting such light, with the use of an optical detector of the optical system, through an edge surface of an internal element of the optical system that is separated from a front surface of the optical system with a front element of the optical system while, at the same time, preventing said light from traversing any surface of the front element. Additionally or in the alternative, in an implementation of the method the internal element may be immediately adjoining the front optical element and/or the step of preventing may include reflecting the light at an annularly-shaped reflective surface that is congruent with a surface of the inner element. Furthermore, the surface of the inner element may be an aspheric optical surface and/or in substantially every implementation of the method, the step of forming the image may include causing the light to interact with three different surfaces of the inner element (here, two of the three different surfaces cross the optical axis and a remaining of the three different surfaces is an edge surface of the inner element).

Alternatively or in addition, and in substantially any implementation of the method, the step of transforming spatial distribution of irradiance may include replacing a first irradiance at a first pixel located along a chosen radius of the image with a second irradiance at a second pixel located along the chosen radius of the image while replacing the second irradiance at the second pixel with the first irradiance at the first pixel. Here, locations of the first and second pixels are symmetric with respect to a circle of a radius that is defined as a weighted combination of (i) a geometric mean of outer and inner radii of the image and (ii) an arithmetic mean of said outer and inner radii.

Embodiments of the invention additionally provide an image of an object space formed with the use of an optical system that has an optical axis, a FFOV, and an LFOV, the image containing (i) a first portion of the image having a first perimeter that circumscribes an axial point of the first image; (ii) a second portion of the image dimensioned as a stripe or band having a second perimeter and located outside of the first perimeter. In such an image, the first portion of the image represents a first portion of the object space covered by the FFOV, the second portion of the image represents a second portion of the object the object space covered by the LFOV, and a first directionality of the first portion of the image and a second directionality of the second portion of the image are the same.

Furthermore, embodiments of the invention provide an optical system having an optical axis, a FFOV) and an LFOV. Such optical system includes a front lens and a rear lens. The front lens is dimensioned to collect only first light from only a first portion of an object space that is covered by the FFOV and forward such first light through the rear lens towards an image plane of the optical system. The rear lens is dimensioned to collect both the first light and second light from a second portion of the object space (the second portion is covered by the LFOV) and image all such light onto the image plane. The optical system also includes at least one optical reflector separating the front lens from the rear lens and configured to reflect said second light towards the rear lens. The optical system is configured to form such an optical image of the object space that includes i) a first portion of the image having a first perimeter that circumscribes an axial point of the first portion of the image; and ii) a second portion of the image dimensioned as a stripe or band having a second perimeter and located outside of the first perimeter. The formed image is such that the first portion of the image represents the first portion of the object space, the second portion of the image represents the second portion of the object the object space, and a first directionality of the first portion of the image and a second directionality of the second portion of the image are the same.

Additionally, embodiments of the invention provide a method for forming an image of the object space with the use of an optical imaging system that has an optical axis, a FFOV, an LFOV, an optical detector, and programmable electronic circuitry operably cooperated with the optical detector, and where the image includes: —a first portion of the image having a first perimeter that circumscribes an axial point of the first image; and—a second portion of the image dimensioned as a stripe or band having a second perimeter and located outside of the first perimeter. Here, there following conditions are met: the first portion of the image represents a first portion of the object space covered by the FFOV, the second portion of the optical image represents a second portion of the object space covered by the LFOV, a first directionality of the first portion of the image and a second directionality of the second portion of the image are the same. The method includes the steps of (a) forming the first portion of the image by collecting first light from the FFOV through both first and second optical elements of the optical system with the use of the optical detector (here, the first optical element is an optical element directly exposed to the first portion of the object space, and the second optical element is immediately adjoining the first optical element); (b) forming, with the use of the optical detector, a third portion of the image by at least in part collecting second light from the LFOV of the optical system through an edge surface of the second element of the optical system while preventing such second light from traversing any surface of the first optical element (here, the third portion of the image is dimensioned as the stripe or band having the second perimeter and located outside of the first perimeter, and a third directionality of the third portion of the image is opposite to the second directionality); (c) transforming irradiance of the third portion of the image to create the second portion of the image by radially redistributing the irradiance of the third portion of the image with respect to a circle of a chosen radius located between inner and outer perimeters of said second portion of the image; and (d) with the use of said programmable electronic circuitry, generating a report or output containing a visually-perceivable representation of the image.

BRIEF DESCRIPTION OF THE DRAWINGS

The invention will be more fully understood by referring to the following Detailed Description of Specific Embodiments in conjunction with the not-to scale Drawings, of which:

FIG. 6A: directionality of portions of an aggregate image acquired with a conventionally-structured system: with advancing the conventional optical system along the optical axis, near objects are imaged to be further outwards from the optical axis, and far objects are seen located closer to the optical axis. FIG. 6B: directionality of portions of an aggregate image acquired with an embodiment of the present invention: with advancing the optical system of the invention along the optical axis, an image of a given object (that is viewed as moving from the front to the rear of the optical system) is relocated from a central area of the image to its peripheral area.

FIGS. 18B, 18C illustrate the spot diagrams and field curves of the embodiment of FIG. 13 (or, otherwise, of the portion of the lens depicted in FIG. 15) associated with imaging of the object space in the LFOV only.

Figure 1:
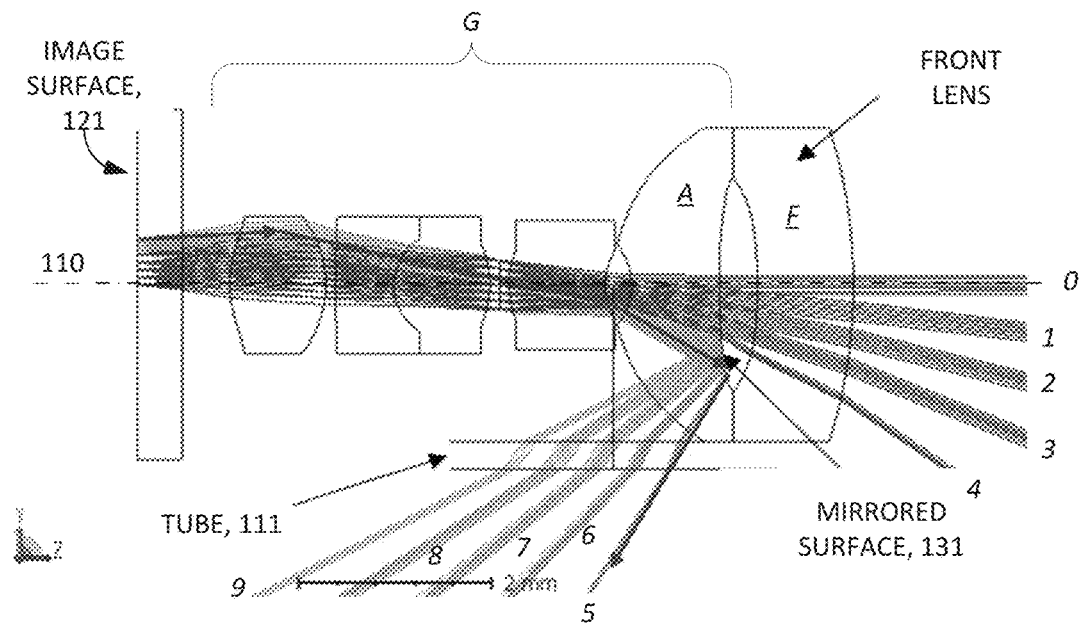
FIG. 1 is a schematic illustration of a lens system configured to enable a formation of a conventional optical image.

Generally, the sizes and relative scales of elements in the Drawings may be set to be different from actual ones to appropriately facilitate simplicity, clarity, and understanding of the Drawings. For the same reason, not all elements present in one Drawing may be necessarily shown in another.

DETAILED DESCRIPTION

The following discussion is aimed at and addresses methodologies for forming an optical image (of an object space) all portions of which remain co-directional regardless of whether these portions are the ones formed in a FFOV and/or an LFOV, and regardless of the mutual repositioning of the image-acquiring optical system and the object space. The imaging methodology generating such results is in stark contradistinction with the formation of an optical image achieved with the use of a conventionally-structured optical imaging system.

For the purposes of the disclosure—and unless expressly stated otherwise, the following terms are used:

The term "object space" is conventionally defined and understood as the space located outside of the optical imaging system in question and a portion of which—referred to as an object—is imaged through the optical imaging system onto an image surface (which may substantially coincide with a surface of an optical detector). It is the space (defined in relation to an optical system), in which the objects to be imaged by the system are located. In comparison, a space that is associated with an optical system and consists of points of which each is an image of a corresponding point in the object space—is the "image space". An object point and its image, formed with the use of the optical imaging system, are considered to be uniquely mapped to one another and, therefore, optically-conjugate to one another.

The term "optically-conjugate" and related terms are understood as being defined by the principal of optical reversibility (according to which light rays will travel along the originating path if the direction of propagation of light is reversed). Accordingly, these terms, as referring to two surfaces, are defined by two surfaces the points of which are imaged one on to another with a given optical system. If an object is moved to the point occupied by its image, then the moved object's new image will appear at the point where the object originated. The points that span optically-conjugate surfaces are referred to and defined as optically-conjugate points. A first layer or pattern is defined as being carried by (or carried on) a given surface or substrate or second layer when the first layer is directly disposed onto the given surface or substrate or second layer, or when the first layer is disposed onto an intervening third layer which, in turn, is disposed onto the given surface or substrate or second layer.

The term "image" refers to and is defined as an ordered representation of detector signals corresponding to spatial positions. For example, an image may be an array of values within an electronic memory, or, alternatively, a visual or visually-perceivable image may be formed on a display device such as a video screen or printer.

The front field of view (FFOV) of an optical system is a field of view defined by a spatially-uninterrupted solid angle such as to include the optical axis of the system and such that light incident onto the optical system from an object within this solid angle is accepted by and transmitted through the optical system to the image surface.

In comparison, the lateral field of view (LFOV) of an optical system is a field of view that is defined by a corresponding distinct solid angle that does not include the optical axis of the optical system while having light incident onto the optical system from an object within such solid angle be accepted by and transmitted through such optical system to the image surface. Notably, when a given optical system has both a FFOV and LFOV, these fields of view spatially differ from one another.

A term "positive direction of an optical axis", as used in reference to a given optical system is defined as a direction or vector representing an orientation of the optical axis from a chosen image space towards the front element of the optical system. For example, when an optical system is used in conjunction with an optical detector located behind the rear element of the optical system, the positive direction of the optical axis is the direction from the optical detector towards the front element of the optical system. (In this case, the negative direction of the optical system would be defined by a vector substantially collinear with the optical axis and pointing from the front optical element of the system towards the optical detector.)

The term "viewing angle" refers to and is defined as an absolute value (modulus) of an angle, measured with respect to and from the positive direction of the optical axis of a given optical system, at which such optical system views or observes a given object point within a FOV of the optical system.

The term "orientation" (used herein to describe an optical image formed in an image plane of the optical system in light arriving from the scene in a given FOV), refers to and is defined by one-to-one correspondence between (and corresponding mapping of) a radial position of an image point (in the optical image) with respect to the optical axis and a viewing angle characterizing an object point that is optically-conjugate with such image point.

Conventionally-structured optical imaging systems having front field-of-view and a lateral field of view possess one common characteristic: images of object space formed light arriving, respectively, from the FFOV and the LFOV of such systems are not co-directional.

For example, in the process of formation of an image of an object in light propagating through a conventionally-structured dioptric optical system, a first object point observed by the optical system at a larger viewing angle corresponds to and forms a first image point located at a first radial distance from the optical axis in the image plane that is larger than a corresponding second radial distance of a second image point formed by another (second) object point observed by the optical system at a smaller viewing angle. Formation of an image in a conventionally-structured catadioptric optical system having an odd number of reflective surfaces is reversed: an image point located farther away from the optical axis represents a corresponding optically-conjugate object point viewed by the system at a smaller viewing angle. A skilled artisan will immediately appreciate this fact by considering, for example, a formation of optical image in a simple single lens element (a dioptic system), or in a complex lens system described in US 2016/0088204 in reference to FIGS. 1 and/or 2 of US 2016/0088204.

FIG. 1 presented here provides an additional schematic illustration of this conventional image formation in the optical system 100 that is enclosed in an optically-transparent tube (only a portion 111 of which is schematically illustrated) such that light from locations 0, 1, 2, . . . 9 in the object space could be collected by the system 100 not only from the portion of the object space in front of the system 100, but also from that portion of the object space located on the sides of the lens system 100. The system 100 includes a combination of lens elements and optical reflectors, and is shown to contains a front lens element F (a dioptric portion of the overall system 100) and a group G of lens elements, of which the one adjacent to the element F (shown as the lens element A) has one of its surfaces partially coated with a reflective coating (a reflector) shaped substantially like a ring to form an odd number of mirrored surfaces (a catadioptric portion of the system 100). As shown, the bundles of light 0, 1, 2, 3, and 4 incident onto an outer surface of the from lens F upon their propagation from the object space to the image surface 121 of the system 100 interact only with reflective optics (thereby contributing to the dioptric image Formation), while the bundles of light 6, 7 . . . 9 incident onto the reflective coating (mirrored surface, 131) from the side of the optical axis 110 of the system 100 form the corresponding image points after interaction with the mirrored surface of the lens A and the refractive optics of the group G of the lens elements (thereby contribution to the catadioptric image formation).

It is appreciated that the formation of an image in the image surface of such system 100 obeys a conventional principle, according to which a portion 0 of the object space viewed by the system 100 at an infinitesimally small (substantially zero) viewing angle has its optically-conjugate portion of the image substantially at the optical axis 110. As shown, the viewing angles corresponding to the portions of the object space giving rise to the bundles of light 1, 2, 3, 4 in the field of view defined by the combination of the optical sub-systems G and F are progressively increasing in value (from that corresponding to the bundle 1 to that corresponding to the bundle 4). At the same time, the portion of the image formed by a light bundle emanating from the portion 1 of the object space is offset from the axis 110 by a first radial distance, while the portion of the image formed by a light bundle 2 emanating from the object portion 2 is displaced from the axis 110 by a second radial distance that is larger than the first radial distance. Similarly, the radial displacement of the image portion formed by the bundle 4 (the one emanating from the object point viewed by the system 100 at the largest viewing angle corresponding to the dioptric image formation) would be the largest among those respectively corresponding to the image points formed by the bundles 0 . . . 4. For the object points forming corresponding image portions with the light bundles 6, 7, 8, and 9 the situation is exactly the one corresponding to the conventional catadioptric image formation in a system with an odd number of reflective surfaces. Specifically, while the viewing angle corresponding to the object point 9 is large than that corresponding to the object point 5, the light bundle 9 emanating from the object point 9 will form a corresponding image point at a smaller radial distance from the axis 110 than that representing the image point formed by the light bundle emanating from the object point 5.

The term "directionality" of a given optical image refers to and is defined by a direction of a change of a position of an image point, in such optical image, with respect to the optical axis as a function of a viewing angle of the corresponding object point in the object space.

Considering a first example of what the directionality of an optical image means, the radial position of an image of an object point A (and initially viewed by the system at a viewing angle α) will be increasing as a result of mutual repositioning of the dioptric optical system and this object point such that the viewing angle of this object point A is increasing from α to α'>α. In this case, the directionality of the optical image containing the image of the object point A is defined by a radial vector, in the image plane, pointing away from the optical axis. That is, in this first example, when the mutual repositioning between the optical system and the object point A leads to increase of the viewing angle and which the optical system observes the object point A, the result caused in the image plane is that the image of point A is moving away from the optical axis.

With that recognized, a skilled artisan will readily understand and appreciate that—in another, second example—a directionality of a given optical image defined by repositioning of an image point along a radius towards the optical axis (in the image plane) and caused by the increase of a viewing angle of the corresponding object point is defined as opposite to the directionality of the image in the previous, first example.

Similarly, if the optical image is such that an image of a first object point (viewed by the optical system at a smaller viewing angle) is positioned farther away from the optical axis in the image surface than an image of a second object point (viewed by the optical system at a larger viewing angle), the directionality of this image is defined as opposite to the directionality of the image in the first example.

When directionalities of the portions of the image that contain, respectively, images of the object points B and C (with the viewing angle for point B being smaller than the viewing angle for point C) are defined in the image surface by respectively-corresponding radial vectors that point in the similar fashion (for example, both away from the optical axis, or both towards the optical axis)—such portions of the image are defined as being co-directional.

With that in mind and referring again to the optical system 100 of FIG. 1, it becomes clear that both the orientation and directionality of a first portion of the image formed by light bundles 0, 1, 2, 3, and 4 through the optical system 100 is, understandably, different from the orientation and directionality of the second portion of the image formed by light bundles 6 . . . 9 through the optical system 100. Similarly, the skilled artisan will immediately recognize that both the orientations and directionalities of the different portions of the aggregate image formed with the use of the optical system of US 2016/0088204 and representing different fields of view of that optical system are not the same and differ from one another as well.

The presentation below is organized as follows. First, based on introduction of the specific type of indicia with which the object space is marked, explanations are provided of how such object space is imaged with a conventionally-structured optical imaging system that conventionally forms not-codirectional images of the object space viewed in the FFOV and the LFOV of such conventional optical system. Then, discussion of implementation of the idea of the invention is presented, differentiating the formation of co-directional optical images in FFOV and LFOV from the conventional not-codirectional image formation.

First, to illustrate more clearly the shortcomings (of imaging of the object space in different FOVs of a conventionally-structured system) that embodiments of the present invention address, it may behoove to consider an object space marked with some characteristic indicia.

(1) Examples of Indicia Used to Mark Object Space.

Consider the situation when a given optical imaging system is disposed inside a tubular member limiting the view of such optical imaging system. Such optical imaging system is configured, according to the idea of the invention, such as to have an FFOV and an LFOV and to have an image formed in light arriving from the FFOV and that formed in light arriving from the LFOV be co-oriented and co-directional. As the skilled artisan will readily appreciate, the results of imaging of the judiciously-marked inside surface of the tubular member with such an optical imaging system are drastically different from the results of imaging of the same inside surface with the conventionally-configured optical system.

Figure 4A:
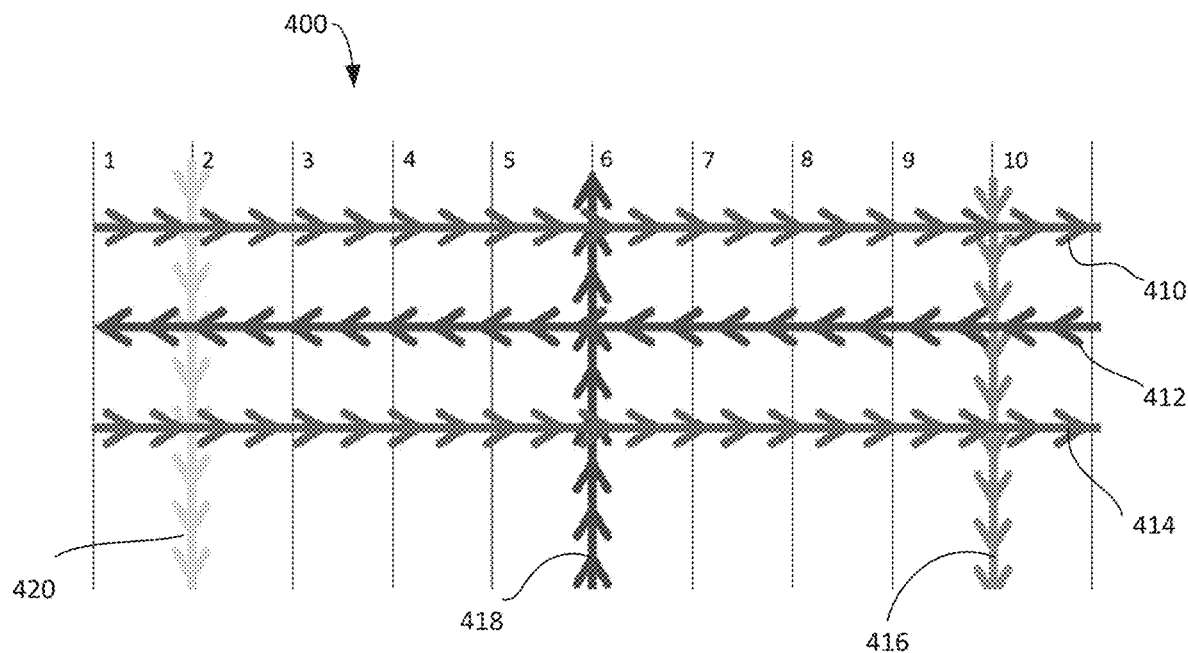
FIGS. 4A, 4B illustrate two types of indicia used for marking an object space for the purposes of optical imaging of same with various lens system.
Figure 4B:
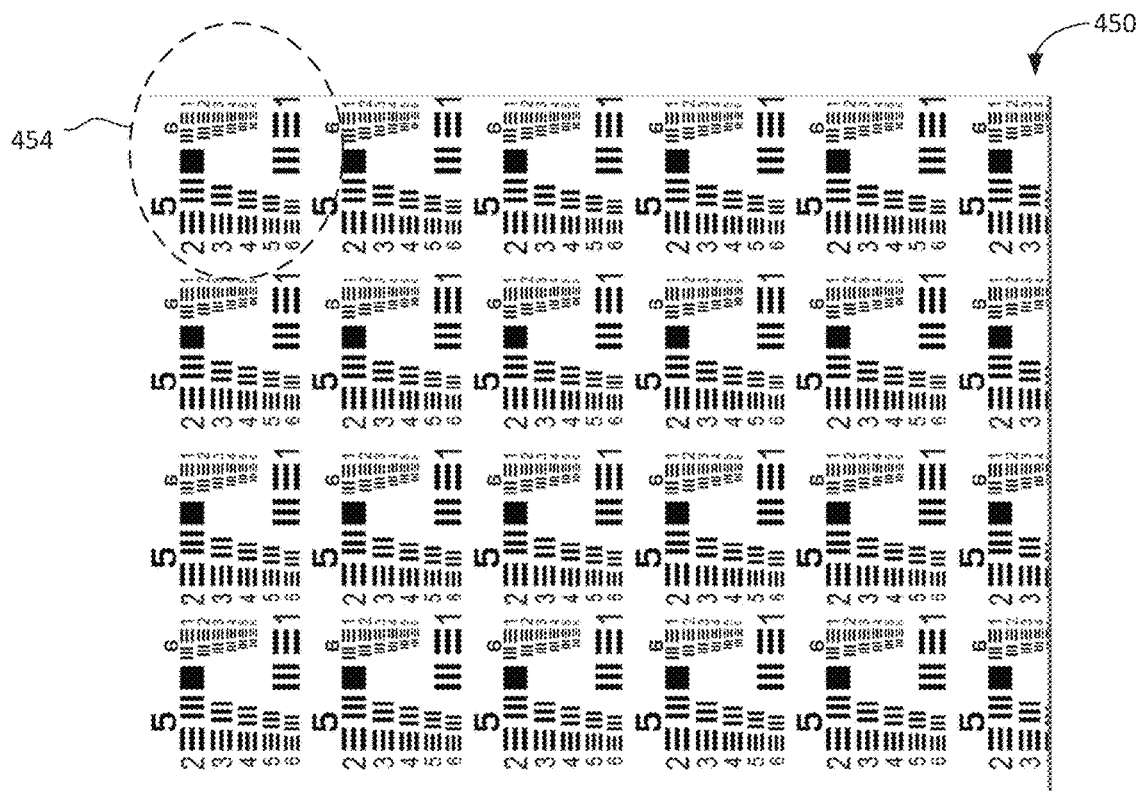

To this end, FIGS. 4A, 4B illustrate two types of indicia 400, 450, with which the inside surface of a cylindrical tube is marked in two different experiments. Each of FIG. 4A and FIG. 4B shows the markings "unwrapped" from the cylindrical inner surface of the corresponding tube onto a planar surface (by analogy with the map of the Earth presented in, for example, a Mercator Projection, with one distinct difference, however, in that the representation of the indicia 400, 450 in FIGS. 4A, 4B does not possess distortions associated with the projections typical to the projections of a sphere on a plane, as will be understood by a skilled artisan). FIG. 4A illustrates the markings 400 that contain the combination of digits 1 through 10 (oriented along the axis of the cylindrical tube and, therefore, along the positive direction of the optical axis of a given optical system inserted in such tube) and the set of arrows 410, 412, 414, 416, 418, 420, as illustrated. With respect to the inner surface of the tube, the arrows 410, 412, 414 run along the tube's axis, while the arrows 416, 418, 420 are organized in circles surrounding the tube's axis and pointing in clockwise and counterclockwise ways. FIG. 4B depicts a different type of markings 450, which represent a matrix of a indicia sub-set 454 repeated multiple times, and disposed on the inner surface of the tubular member. (The sub-set 454 in this example is but a well-known 1951 US Air Force resolution test chart, or target, and contains subsets of three lines of gradually decreasing thickness. The lines are subdivided into groups and sets. Each set consist of a subset of three vertical lines and a subset of three horizontal lines. See en.wikipedia.org/wiki/1951_USAF_resolution_test_chart for reference.) Notably, such indicia can be used with any implementation of any optical system to identify the directionality of the formed image(s).

(2) Formation of not-Co-Directional Images of the Identified Indicia with the Use of a Conventionally-Structured Optical System.

Figure 5A:
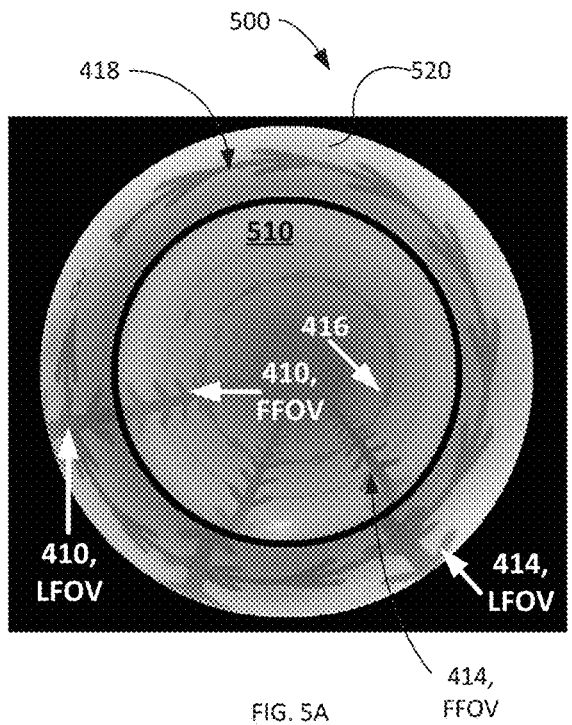
FIGS. 5A, 5B are images of an object space marked with indicia of FIGS. 4A, 4B, formed with an embodiment of a conventional lens system of related art.
Figure 5B:
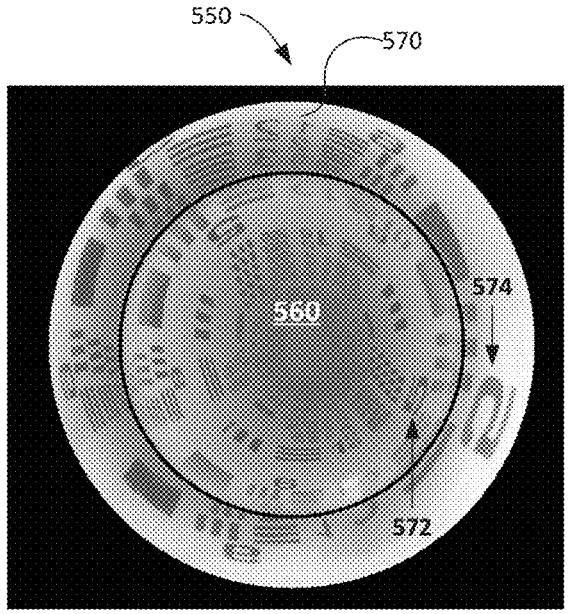

FIGS. 5A, 5B schematically illustrate aggregate images 500, 550, formed by imaging the object space marked with, respectively, indicia 400 and 450 with the embodiment of the optical system of US 2016/0088204 or any other conventionally-structured optical system of related art (for example, an optical system schematically depicted in FIG. 1).

The aggregate image 500 includes two image portions 510 (representing the imaging of the target 400 covered by the FFOV of the optical system of the related art) and 520 (representing the imaging of the target 400 covered by the LFOV of the same optical system of the related art). The arrow 416 and the digits 9, 10 are seen by the conventionally-structured optical system only in the FFOV, and therefore are imaged only into the portion 510 of the image 500. The arrow 418 and the digit 6 are viewed by the optical system of related art only in the LFOV, and, therefore, are imaged only into the image portion 520. Arrows 410, 412, 414 are observed in both FFOV and LFOV and, therefore are imaged into both image portions 510 and 520 of the image 500.

Figure 6A:
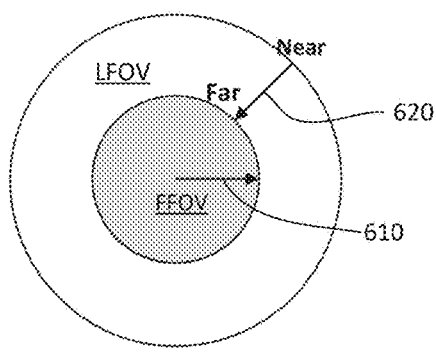
FIGS. 6A, 6B illustrate counter-directional and co-directional portions of an aggregate image representing optical information acquired both in the FFOV and the LFOV of a given optical imaging system. Central portion of the image is that acquired in the FFOB; the surrounding (shown as annular) portion—that acquired in the LFOV. Portions of the image are separated with a closed planar curve.

It can be easily recognized that the orientation of the image portions 510, 520 are opposite to one another (as seen by the orientations of the digit 6, arrows 410, 414 in the LFOV-based image portion 520 in comparison with those in the FFOV-based image portion 510). The skilled artisan will immediately understand and appreciate that the directionalities of the image portions 510, 520 are also opposite to one another: when the optical system discussed in the US 2016/0088204, for example is moved along the optical axis inside the marked as described tubular member (the object space) in a positive direction of the optical axis, a given image point in the image portion 510 is repositioned towards the perimeter of the image field (along the arrow 610 of FIG. 6A), while another given image point in the image portion 520 is repositioned towards the center of the image field (along the arrow 620 of FIG. 6A). A person of skill will all readily appreciate and agree that similar performance (that is, formation of images of opposite orientation and directionality in the different fields of view) is demonstrated by substantially any optical system of related art, including that depicted in the schematic example 100 of FIG. 1.

Similarly, the aggregate image 550 of the object space (tubular member) marked with indicia 450, formed with the conventionally-structured optical imaging system (such as the system of the US 2016/0088204, for example), includes two image portions 560 and 570. These image portions contain respective images of the object space (the inner surface of the tubular member) in the FFOV and LFOV, respectively. The different orientations of these image portions can be clearly identified by comparing spatial orientations of the elements 572, 574 of the indicia (both of which are represented by a digit 5). A person of skill will immediately recognize that the directionalities of the image portions 560, 570 are also opposite to one another: when the optical system discussed in the US 2016/0088204 is moved along the optical axis inside the marked-as-described object space in a positive direction of the optical axis, a given image point in the image portion 560 is repositioned towards the outer perimeter of the image field (along the arrow 610 of FIG. 6A), while another given image point in the image portion 570 is repositioned towards the center of the image field (along the arrow 620 of FIG. 6A). Moreover, a person of skill will now readily appreciate and agree that similar performance (that is, formation of images of opposite orientation and directionality in different fields of view) is demonstrated by substantially any optical system of related art, including that depicted in the schematic example 100 of FIG. 1.

(3) Solutions Provided by Embodiments of the Invention.

A problem of forming an optical image with the use of a conventionally-structured optical system having multiple FOVs (which problem manifests in forming such image the different portions of which have opposite to one another directionalities) is solved by providing a catadioptric lens system having an odd number of optical reflectors and configured such that—regardless of the location of a given object point with respect to the optical axis of the lens system—an object point viewed by the system at a larger viewing angle is optically-mapped to an image point at a farther from the axis radial coordinate in the image plane (and vice versa), while an object point viewed at a smaller viewing angle is mapped to an image location at a smaller radial separation from the axis (and vice versa).

Moreover, a problem of inability of optical imaging systems of related art to define optically-conjugate object and image points (during optical imaging of the object space) such that an object point viewed by the optical imaging system at a larger viewing angle is uniquely mapped to and represented by an image point located at a radial distance (from the optical axis) in the image plane that is larger than a corresponding radial distance of an image point representing another object point viewed by the same system at a smaller viewing angle, is solved by incorporating into the optical imaging system a spatially-discontinuous reflector with a spatial profile that depends on and is derived from the function of a viewing angle, according to which the object points of interest are distributed around the optical imaging system. (In different practical implementations, one being discussed below in Example 1, such spatial profile of the reflective surface—involute surface—may be judiciously defined by a spline function that is constructed piecewise by polynomials and/or is not an analytic function—that is, a function that cannot be represented by a convergent power series. Accordingly, as understood by a skilled person, a reflector defined by such involute reflective surface or layer is not a ring reflector.) As a result of the use of so-defined reflector having an involute reflective surface, an embodiment of the optical system of the invention operates by mapping an object point located, in the lateral FOV, at (corresponding to) smaller viewing angle to a corresponding image point located in the image plane at a smaller radial distance from the optical axis (and vice versa). At the same time, the embodiment of the optical system of the invention transmits light—that arrives from the objects points in the front FOV through a spatial discontinuity of (an optical aperture in) the involute reflective surface—to miss and not cross the involute reflective layer and to map an object point located, in the front FOV, at a larger viewing angle to a corresponding image point located in the image plane at a larger radial distance from the optical distance (and vice versa). As a result, any object point—whether imaged with the use of the involute reflective surface/layer or without involving such involute surface/layer—is mapped to a uniquely corresponding optically-conjugate image point having a radial coordinate that is monotonic with the change of the viewing angle.

Below, several examples of the optical imaging methodologies are discussed, the implementation of each of which achieves the same goal—a formation of an optical image formed in both FFOV and LFOV of the optical imaging system, with respective portions of the optical image remaining co-directional regardless of a change of the position of the optical imaging system with respect to the object space.

Embodiments of the invention may be interchangeably referred to herein as multi-view imaging devices (MVIDs).

Example 1: Creation of Co-Oriented and Co-Directional Images as a Direct, Immediate Result of Optical Imaging of Object (without Transformation of the Formed Image)

As a result of configuring an embodiment of a catadioptric optical system having an odd number of reflectors and more than one field of view (one of which may be a FFOV and another may be an LFOV) such that an object point viewed by the system at a larger viewing angle is optically-mapped to an image point at a farther from the axis radial coordinate in the image plane (and vice versa), while an object point viewed at a smaller viewing angle is mapped to an image location at a smaller radial separation from the axis (and vice versa)—different portions of the aggregate image that represent portions of object space viewed in different fields of view of the optical system at hand are co-directional (that is, possess the same directionality). One practical advantage of the proposed solution becomes immediately apparent when imaging an object that represents an inner surface of a generally tubularly-shaped ambient environment from inside such environment (the object space an example of which was introduced above)

Incidentally, as used in this application and unless expressly defined otherwise, the terms "lenslet" and "lens element" are defined to refer to a single, simple, structurally-indivisible and used singly optical component that changes the degree of convergence (or divergence, or collimation) of light passing through or traversing such component. In comparison, the terms "lens", "group of lenses", "lens system" and similar terms are defined to refer to a combination or grouping of lenslets or lens elements. Here, the optical doublet, for example, which is made up of two simple lenslets or lens elements paired together, is considered to be a lens.

Figure 2B:
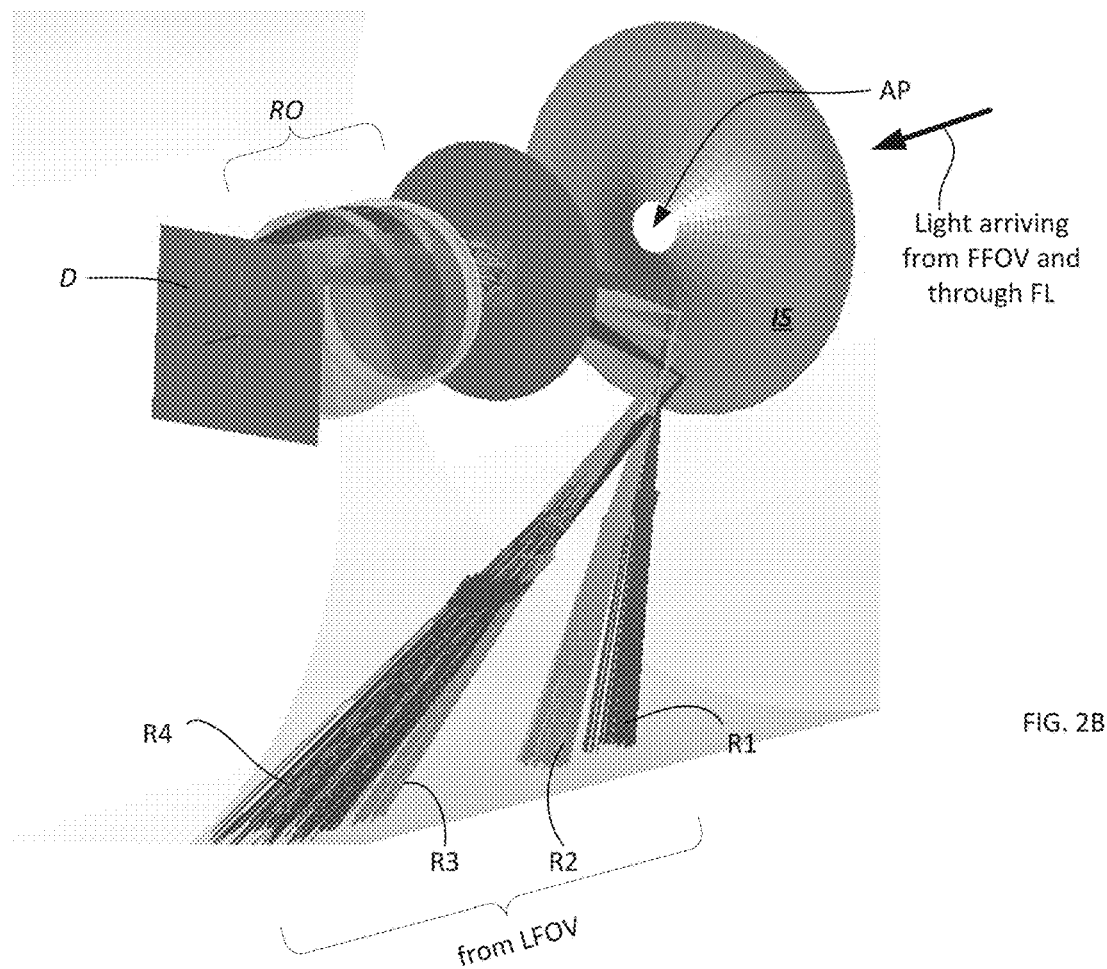
FIGS. 2A, 2B are schematics of an embodiment of the lens system configured according to an idea of the invention.
Figure 2A:
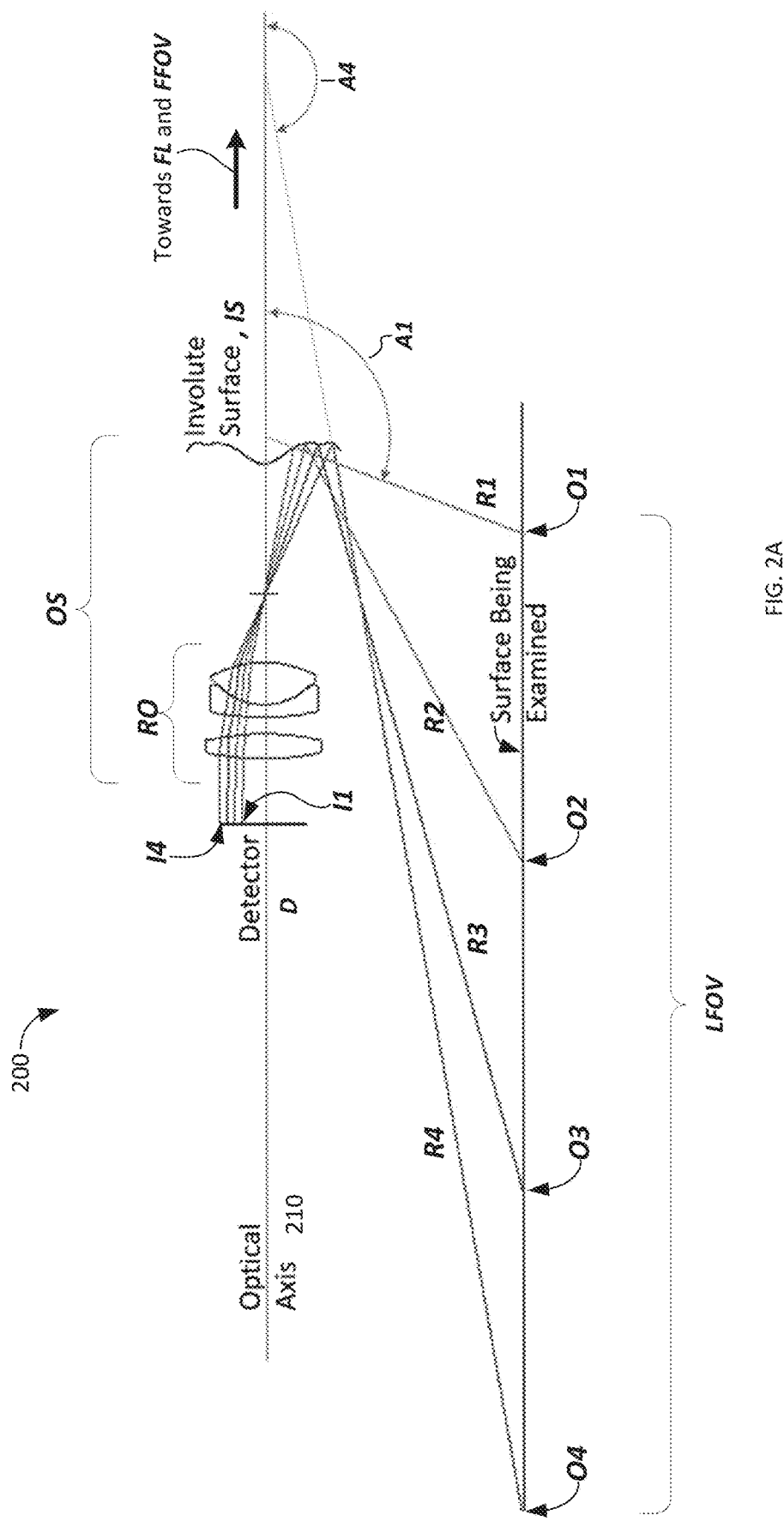

The principle of the employed solution is schematically illustrated in FIG. 2A. Here, a portion OS of the overall optical imaging system 200 is shown, which includes a portion OS and a front lens FL of the system 200 disposed in front of the portion OS. (The presence of the lens FL is indicated with a corresponding pointing arrow). The portion OS includes an involute reflector IS and a refractive optics RO. The involute reflector IS has a non-reflective aperture or an opening around the optical axis (not necessarily shown in FIG. 2A.

Light acquired by the imaging system 200 through the front lens FL from the FFOV and transmitted through the aperture AP in the reflector IS and through portion OS to the optical detector D forms an image that represents the portion of the object space seen by the system 200 within the FFOV.

The portion OS by itself is configured to image a portion of the object space covered by the LFOV—and, in particular, object points O1 through O4 located on a surface wrapping around the optical axis (which may be, in one instance, a generally-tubular surface) onto the optical detector D with the use of the refractive optics RO (shown here to include a group of lenses and/or elements) after being reflected from the involute reflective surface IS. In operation, the portions OS and FL of the overall system 200 are imaging portions of object space covered by the LFOV and the FFOV o the system 200.

Referring now to the portion OS of the imaging system 200, rays R1, R2, R3, and R4, representing such light are shown to originate at the respectively-corresponding object space points O1, O2, O3, and O4 and directed through the optics RO after being reflected from the involute reflective surface IS. The spatial mapping of the object points O1 through O4 onto the sensitive surface of the detector D (which is configured as the image plane) is accomplished according to the corresponding viewing angles at which the optical system views these object points. Here, the corresponding viewing angles A1, A2, A3, A4 are progressively increasing: A1<A2<A3<A4 (only A1 and A4 are expressly indicated in FIG. 2A). This spatial mapping between the object and image spaces is configured such that the radial coordinate of the image 14 of the point O4 is larger than the radial coordinate of the image I3 of the point O3, which is larger than the radial coordinate of the image I2 of the point O2, which in turn is larger than the radial coordinate of the image I1 of the point O1. In FIG. 2A. only two image points are expressly indicated for simplicity of illustration: points I1 and I4.

FIG. 2B schematically illustrates the portion OS of the optical system 200 in a perspective view, where the non-reflective (and transmissive) aperture AP, defining the spatial discontinuity in the involute reflector IS, is expressly indicated and is used to collect and image light arriving from the portion of the object space covered or viewed by the FFOV of the overall system 200 through the front lens FL. Here, the surface of the involute reflector IS itself is shown to collect and redirect through the refractive optics RO light that arrives from the portion of the object space covered by the LFOV of the overall optical imaging system of FIG. 2A.

Figure 3:
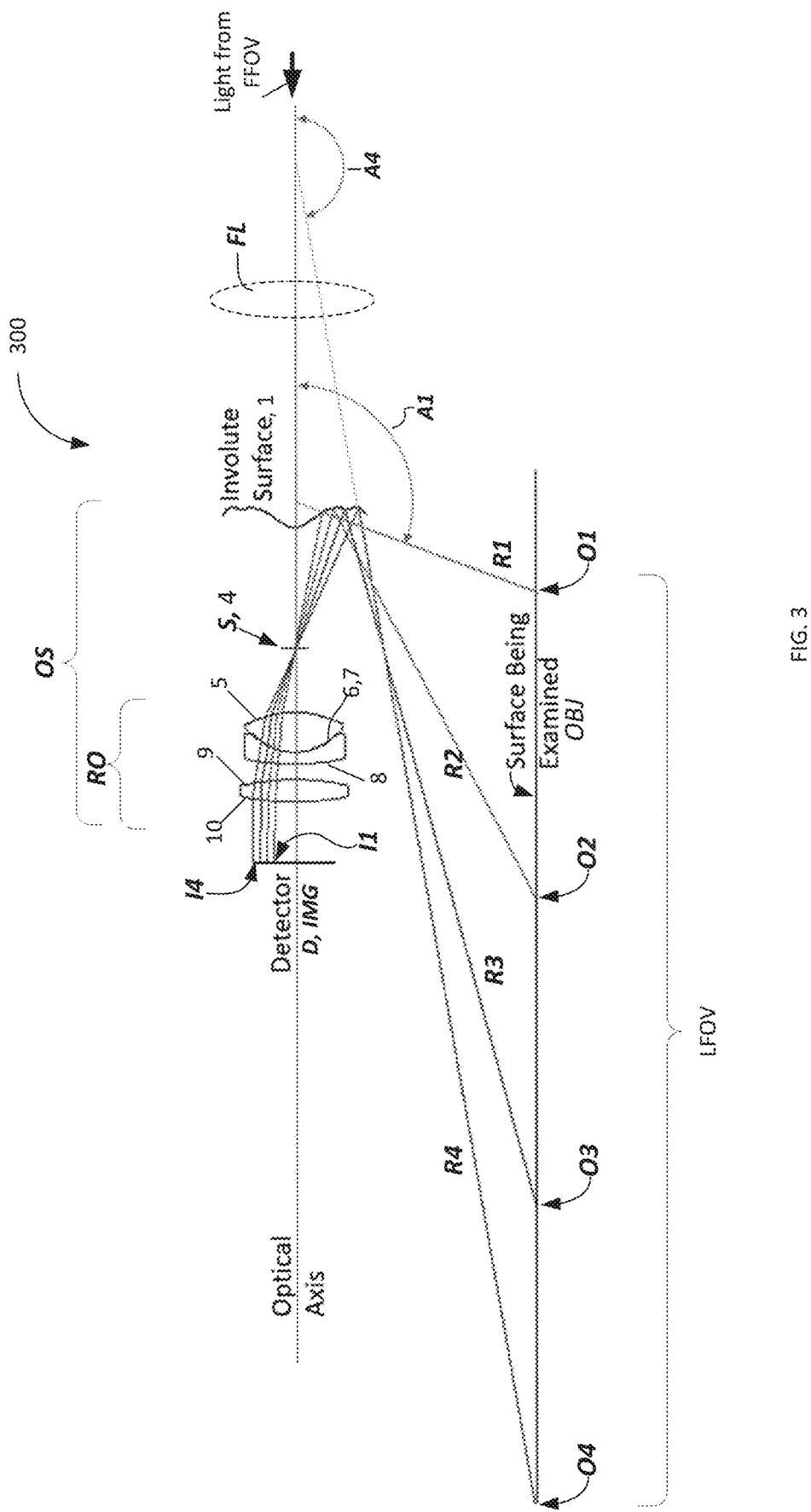
FIG. 3 is a perspective view of the embodiment of FIGS. 2A, 2B.

A specific non-limiting embodiment 300 of the overall system 200 is schematically illustrated in FIG. 3. Here, the front lens FL is explicitly shown to complement the optical portion OS. In reference to FIG. 3, the reflective optical RO is shown as a lens behind the front lens FL, and separated from the front lens FL with the involute reflective surface IS. The description of one non-limiting implementation of the optical portion OS includes Table 1.1 summarizes the opto-geometrical characteristics of the OS-portion of the system 300. For simplicity of illustration, the axially-symmetric aperture AP in the reflector IS (having diameter of about 5 mm and visible in FIG. 2B) is not shown in FIG. 3.

In reference to Table 1.1, numbering of the optical elements and optical surfaces is specific to FIG. 3 only. Light within the range of viewing angles of the system 300 that corresponds to the LFOV arrives at the IS reflector (surface 1 of the design, see Table 1.1) that is configured to reflect this light through the rear lens RO only, to form an image IMG of the portion of the object space covered by the LFOV on the detector D. Upon propagation towards the first subset of the rear lens RO—which first subset in this example is the optical doublet formed by the optical lens elements with surfaces 5, 6, 7, and 8—light from the LFOV passes through the aperture stop (5, surface 4) of the system 300 separated from the surface 5 by 2 mm. As shown, one surface of the optical doublet is chosen to be an aspherical surface. The rear lens RO is complemented with the substantially spatially-symmetric lenslet having the optical surfaces 9 and 10, which is separated from the image plane by about 2 mm.

A skilled artisan will appreciate that introduction of the dummy surfaces 2 and 3 in this design is required by the nature of the optical design software (Code V in this case). In further reference to FIG. 3, the optical reflector IS is shown to be a stand-alone optical reflector—that is, an optical reflector that is spatially-separated by a non-zero distance from the nearest refractive optical elements. In this embodiment, the spatial profile of the involute optical reflector IS (in a plane containing the optical axis) is defined piecewise by polynomials and, therefore, is chosen to be represented by a spline function that—while being a function of the viewing angle of the optical system—is not an analytic function of such viewing angle. It is appreciated that the process of optical imaging of the object space portion covered by the LFOV may possess a certain amount of astigmatism, since the curvatures of the spatial profile of the involute reflector IS may not be necessarily the same in the plane containing the optical axis of the system 300 and in a plane transverse to the optical axis.

TABLE 1.1

| ELT NO. | SUR NO. | SURFACE DESCRIPTION | | | THICKNESS OR SEPARATION | APERTURE DESCRIPTION | | | MATERIAL |
|---|---|---|---|---|---|---|---|---|---|
| | | RADIUS | | | | DIMENSION | | | |
| | | X | Y | SHAPE | | X | Y | SHAPE | |
| OBJ (object) | | INF | | FLT | 8.0000 | | | | AIR |
| | | | | | −5.1000 | 24.545 | | CIR | |
| | | REVERSE DECENTER(1) | | | | | | | |
| | | DECENTER(2) | | | | | | | |
| | | | | | 11.2106 | 54.617 | | CIR | |
| 1 | 1 | INF | INF | S-1 | −11.2106 | 5.017 | | CIR | REFL |
| | | | | | 7.2000 | 7.637 | | CIR | |
| | | REVERSE DECENTER(3) | | | | | | | |
| 2 | 2 | INF | | M-1 | 0.0000 | 0.889 | | CIR | AIR |
| 2 | 3 | INF | | M-1 | −0.2500 | 0.860 | | CIR | AIR |
| S | 4 | | | | −2.0000 | 0.717 | | CIR | (STOP) |
| 3 | 5 | −3.038 | | A-1 | −1.3000 | 3.344 | | CIR | E48R Zeon |
| 3 | 6 | 2.000 CX | | SPH | 0.0000 | 3.338 | | CIR | |
| 4 | 7 | 2.000 CC | | SPH | −0.4000 | 3.338 | | CIR | OKP4HT Osaka |
| 4 | 8 | 6.894 CX | | SPH | −0.5000 | 3.696 | | CIR | AIR |
| 5 | 9 | −7.985 CX | | SPH | −0.7500 | 3.904 | | CIR | E48R Zeon |
| 5 | 10 | 7.985 CX | | SPH | −2.0000 | 3.892 | | CIR | AIR |
| IMG (IMAGE) | | INF | | FLT | | 3.121 | | | |

NOTES

Positive radius indicates the center of curvature is to the right

Negative radius indicates the center of curvature is to the left

Dimensions are given in millimeters

Thickness is axial distance to next surface

Image diameter shown above is a paraxial value, it is not a ray traced value

Other glass suppliers can be used if their materials are functionally equivalent to the extent needed by the design; contact the designer for approval of substitutions.

TABLE 1.1-continued

ASPHERIC CONSTANTS $$Z = \frac{(CURV)Y^2}{1 + (1 - (1 + K)(CURV)^2 Y^2)^{1/2}} + (A)Y^4 + (B)Y^6 + (C)Y^8 + (D)Y^{10}$$

| ASPHERIC | CURV | K | A | B | C | D |
|---|---|---|---|---|---|---|
| A-1 | −0.32920849 | 0.00000000 | 1.05132E−02 | −6.60070E−04 | .00000E+00 | 0.00000E+00 |

LENS MODULE SURFACE

| M-1 | | | |
|---|---|---|---|
| | Lens Module | | |
| | Focal Length | (MFL) | 5.500000 |
| | Reduction Ratio | (MRE) | 1.00E+10 |
| | Front Focal Distance | (MFF) | −5.500000 |
| | Back Focal Distance | (MBF) | 5.500000 |
| | Entrance Pupil Distance | (MEN) | 0.000000 |
| | Entrance Pupil Diameter | (MED) | 1.000000 |
| | Semi-field Angle (degrees) | (MFD) | 0.000000 |
| | Chromatic Aberrations: No Chromatic Aberration | | |

SPECIAL SURFACES (SPS types)

S  Curvature = 0.000000E+00
Coefficients for an Extended Spline Surface (SPS ESP)

| SP0 (C1): | 1.0500E+00 | SP1 (C2): | 1.0500E+00 | SP2 (C3): | 8.5652E−01 |
|---|---|---|---|---|---|
| SP3 (C4): | 5.5000E−01 | SP4 (C5): | 2.5252E−01 | SP5 (C6): | 1.3000E−01 |
| SP6 (C7): | −9.0000E−02 | SP7 (C8): | −9.0000E−02 | HT1 (C37): | 4.0000E−01 |
| HT2 (C38): | 8.4000E−01 | HT3 (C39): | 1.2800E+00 | HT4 (C40): | 1.7200E+00 |
| HT5 (C41): | 2.1600E+00 | HT6 (C42): | 2.6000E+00 | HT7 (C43): | 3.0400E+00 |

DECENTERING CONSTANTS

| DECENTER | X | Y | Z | ALPHA | BETA | GAMMA | |
|---|---|---|---|---|---|---|---|
| D(1) | 0.0000 | 0.0000 | 0.0000 | −90.0000 | 0.0000 | 0.0000 | (REVE) |
| D(2) | 0.0000 | 0.0000 | 0.0000 | 0.0000 | 0.0000 | 0.0000 | |
| D(3) | 0.0000 | 0.0000 | 0.0000 | 0.0000 | 0.0000 | 0.0000 | (REVE) |

A decenter defines a new coordinate system (displaced and/or rotated) in which subsequent surfaces are defined. Surfaces following a decenter are aligned on the local mechanical axis (z-axis) of the new coordinate system. The new mechanical axis remains in use until changed by another decenter. The order in which displacements and tilts are applied on a given surface is specified using different decenter types and these generate different new coordinate systems; those used here are explained below. Alpha, beta, and gamma are in degrees.

DECENTERING CONSTANT KEY:

| TYPE | TRAILING CODE | ORDER OF APPLICATION |
|---|---|---|
| DECENTER | | DISPLACE (X, Y, Z) |
| | | TILT (ALPHA, BETA, GAMMA) |
| | | REFRACT AT SURFACE |
| | | THICKNESS TO NEXT SURFACE |
| REVERSE DECENTER | REVE | REFRACT AT SURFACE |
| | | TILT (−GAMMA, −BETA, −ALPHA) |
| | | DISPLACE (−Z, −Y, −X) |
| | | THICKNESS TO NEXT SURFACE |

REFERENCE WAVELENGTH = 550.0 NM
SPECTRAL REGION = 460.0−680.0 NM

This is a non-symmetric system. If elements with power are decentered or tilted or have user-defined or CAD surfaces, the first order properties as determined from the paraxial ray trace may be inaccurate. Use Tools > Macro Manager . . . Sample Macros > 1st Order Analysis > FirABCD to compute the 1st order parameters via an ABCD matrix method.

| INFINITE CONJUGATES | X | Y |
|---|---|---|
| EFL = | −3.4973 | −3.4973 |
| BFL = | −4.1765 | −4.1765 |
| FFL = | 9.9683 | 9.9683 |
| F/NO = | 7.5083 | 7.5083 |

AT USED CONJUGATES

| REDUCTION = | 0.1946 | 0.1946 |
|---|---|---|
| FINITE F/NO = | 7.6727 | 7.6727 |

TABLE 1.1-continued

| | | |
|---|---:|---:|
| OBJECT DIST = | 8.0000 | 8.0000 |
| TOTAL TRACK = | 2.9000 | 2.9000 |
| IMAGE DIST = | −2.0000 | −2.0000 |
| OAL = | −3.1000 | −3.1000 |
| PARAXIAL | | |
| IMAGE HT = | 0.0000 | 0.5409 |
| IMAGE DIST = | −4.8573 | −4.8573 |
| SEMI-FIELD | | |
| ANGLE = | 0.0000 | 61.8740 |
| ENTR PUPIL | | |
| DIAMETER = | 0.4658 | 0.4658 |
| DISTANCE = | 10.3603 | 10.3603 |
| EXIT PUPIL | | |
| DIAMETER = | 4.1560 | 4.1560 |
| DISTANCE = | 27.0277 | 27.0277 |

NOTES
FFL is measured from the first surface
BFL is measured from the last surface The spatial profile of the involute surface (IS, 4)—which in the specific case of the embodiment 300 is shown to be rotationally-symmetric about the optical axis—is judiciously defined by a spline function that is constructed piecewise by polynomials and is not an analytic function. See "special surfaces" in Table 1.1. (Accordingly, as understood by a skilled person, a reflector defined by such involute reflective surface is not a ring reflector.) As a result of the use of so-defined reflector having an involute reflective surface IS, the embodiment 300 operates by optically mapping an object point located, in the lateral FOV, at (corresponding to) a smaller viewing angle to a corresponding image point located in the image plane IMG at a smaller radial distance from the optical axis (and vice versa). At the same time, the embodiment 300 transmits light collected from the objects points in the front FOV by the front lens FL through a spatial discontinuity of (optical aperture AP in) the involute reflective surface IS such as to not impinge onto (not cross, not interact with) the involute reflective surface and to optically map an object point located, in the front FOV, at a larger viewing angle to a corresponding image point located in the image plane at a larger radial distance from the optical axis (and vice versa). As a result, any point of the object space that can be imaged with the use of the system 200 (and whether covered by the LFOV or the FFOV and whether imaged with the use of the involute reflective surface through the rear lens RO or without involving a reflection of light off of involute surface and through both lenses FL and RO) is optically mapped to a uniquely corresponding optically-conjugate image point having a radial coordinate that changes monotonically with the viewing angle of the object point. Specifically, as the value of the viewing angle at which the system 300 observes a portion of the object space increases, the radial distance from the optical axis at which an image of such portion of the object space is formed increases as well, throughout the full range of the available viewing angles.

Images of the Identified Indicia Formed with the Optical System of Example 1.

It is understood, therefore, that in stark contradistinction with the operation of the optical system(s) of related art (such as the embodiment of FIG. 1, for example, or that of US 2016/0088204), the embodiment 300 of the present invention is configured to form different aggregate image of the object space, in which sub-images corresponding to the FFOV and the LFOV are both co-oriented and co-directional.

Figure 7A:
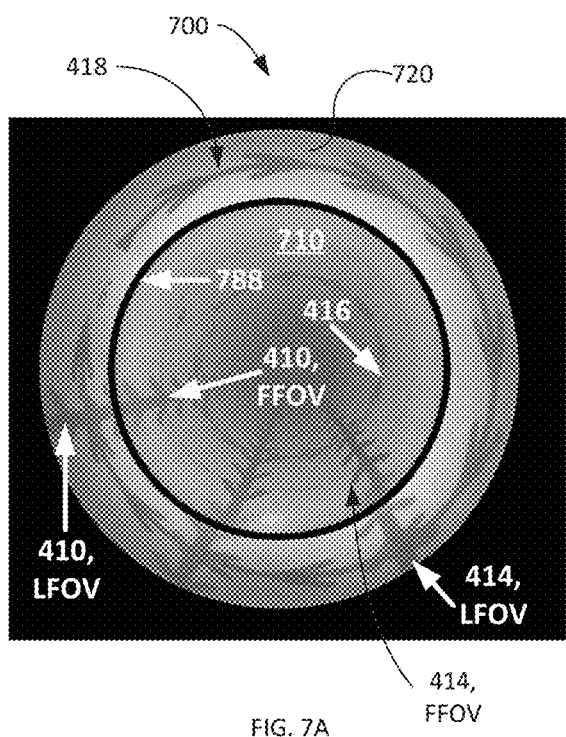
FIGS. 7A, 7B are images of an object space marked with indicia of FIGS. 4A, 4B and formed with an embodiment of an optical imaging system configured according to the idea of the invention.
Figure 7B:
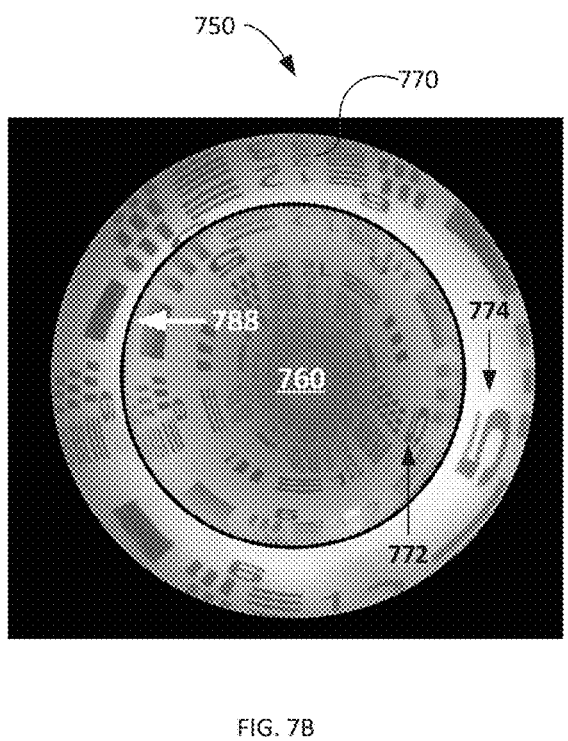

FIGS. 7A, 7B illustrate aggregate images 700, 750, formed by imaging of the object space (marked with, respectively, indicia 400 and 450) with the embodiment 300. The central portions 710, 760 of the images 700, 750 represent the portions of the object space viewed by the system 300 in its corresponding FFOV, while the annular portions 720, 770 of the images 700, 750 represent the portions of the object space viewed by the system 300 in its corresponding LFOV.

Specifically, and in reference to FIG. 7A, the aggregate image 700 includes two image portions 710 (representing the imaging of the target 400 covered by the FFOV of the optical system 300) and 720 (representing the imaging of the target 400 covered by the LFOV of the same optical system). At the chosen position of the optical system 300 within the tubular member carrying the identified indicia on its inner cylindrical surface, the arrow 416 and the digits 9, 10 of the indicia are seen by the optical system 300 only in the FFOV, and therefore are shown to be imaged only into the central image portion 710. The arrow 418 and the digit 6, on the other hand, are viewed by the optical system 300 only in the LFOV and, therefore, are imaged only into the image portion 720 surrounding the image portion 710. Arrows 410, 412, 414 that extend along the axis of the tubular member are observed in both FFOV and LFOV and, therefore are imaged into both image portions 710 and 720.

Figure 6B:
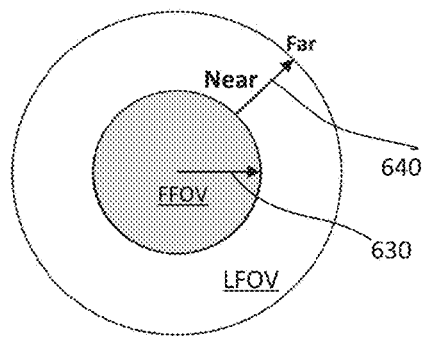

It can be easily recognized that the orientations of the image portions 710, 720 are exactly the same (as seen by the orientations of the digit 6, arrows 410, 414 in the LFOV-based image portion 720 in comparison with those in the FFOV-based image portion 710). The skilled artisan will immediately understand and appreciate that the directionalities of the image portions 710, 720 are also the same: when the optical system 300 is repositioned/moved along the optical axis inside the marked as described object space in a positive direction of the optical axis, a given image point in the image portion 710 is repositioned towards the outer perimeter of the image field (along the arrow 630 of FIG. 6B), while another given image point in the image portion 720 is repositioned also away from the center of the image field (along the arrow 640 of FIG. 6B).

Similarly, and referring now to FIG. 7B, the aggregate image 750 of the object space marked with the pre-defined indicia 450, formed with the embodiment 300, includes two image portions 760 and 770. These are the images of the object space in the FFOV and LFOV, respectively. The equal orientations of these image portions can be clearly identified by comparing spatial orientations of the elements 772, 774 of the indicia (both of which are represented, for example, by a digit 5). A person of skill will immediately recognize that the directionalities of the image portions 760, 770 are also the same: when the optical system 300 is moved along the optical axis inside the marked as described object space in a positive direction of the optical axis, a given image point in the image portion 760 is repositioned towards the outer perimeter of the image field (along the arrow 630 of FIG. 6B), while another given image point in the image portion 770 is repositioned towards the center of the image field (along the arrow 640 of FIG. 6B).

Example 2: Creation of Co-Oriented and Co-Directional Images as a Result of Transformation of the Acquired Optical Image With appreciation of the fact that none of the currently-employed in industry multi-FOV optical imaging systems are configured to possess the ability to form co-oriented and/or co-directional images of the object space in different fields-of-view, there remains a need to ensure that the images produced by such conventional systems can be appropriately transformed into new images that satisfy these criteria.

Accordingly, a problem of visual perception of sub-images that are formed—as not co-oriented and not co-directional portions of the overall, aggregate image—in different fields of view as by a multi-FOV optical system is solved by transforming the spatial distribution of irradiance in at least one of such sub-images to create different spatial distributions of irradiance that satisfy the co-oriented/co-directional criteria. According to the idea of the invention, this transformation is achieved, at least in part, by rearranging, remapping the spatial distribution of irradiance in and image of the LFOV with respect to the identified reference circle of a pre-defined radius. The use of this embodiment of the invention enables the use to transform the not co-direction and/or not co-oriented sub-images of the FFOV and LFOV, generated with the use of a conventionally-structured system, into the sub-images that are co-oriented and co-directional.

Example 2.1 of an Optical System Used with an Embodiment of the Invention

Several notes are in order concerning a particular embodiment of the utilized lens system. Table 2.1 summarizes data representing an optical train (sequence) 1300 of lens elements schematically shown in FIG. 13 and used for imaging of the ambient space in the FFOV. (The imaging of the FFOV involves transmission of light from the FFOV—see schematic rays 1310 and also FIG. 14—through each and every lens element of the optical train 1300). At the same time, the sub-set 1320 of the optical train 1300 is configured, as discussed below, for imaging of the ambient space in the LFOV (see schematic rays 1330, FIG. 15, and Table 2.2). The optical axis of the lens system is denoted as 1340.

The design prescriptions for the embodiments were generated with Code V and are discussed in reference to corresponding figures. In Tables 2.1 and 2.2, optical elements and, possibly, media separating some of the elements, are numbered in a "backward" fashion, starting from that which is the closest to the object/target plane towards the plane of the optical sensor 1350. Such approach to numbering of the optical elements makes it easier, as would be appreciated by a skilled artisan, to define the numerical aperture (NA) during the process of optical design. For example, the closest to the FFOV ambient space object lens element is labeled as element 1 both in Table 2.1 and FIG. 14; the next lens elements is element 2, and so on, while the plane of the optical sensor is referred to as the image plane and labeled as "l". Positive radius value for a given surface indicates that the center of curvature of such surface is to the right of the surface, while a negative radius value indicates that the center of curvature is to the left of the surface; dimensions are provided in millimeters; thickness is defined as an axial distance from a given surface to the next surface; and an indicated image diameter is a paraxial value and not a ray-traced value. Furthermore, with respect to decentering constants (if any), a decenter defines a new coordinate system (displaced and/or rotated) in which subsequent surfaces are defined. In such a case, surfaces following a decenter are aligned on the local mechanical axis (z-axis, for example) of the new coordinate system. The new mechanical axis remains in use for referencing purposes until expressly changed by another decenter. The order in which displacements and tilts are applied to a given surface is specified using different decenter types and these generate different new coordinate systems; those used in this disclosure are explained below. Alpha, beta, and gamma values are presented in degrees. Aspheric surfaces, if any, are labeled as A(i), and the aperture stop is denoted as S. Notations (both in drawings and description) referring to "R", "G", and "B" refer to wavelengths of about 643.85 nm, 546.1 nm, and 479.99 nm.

Figure 14:
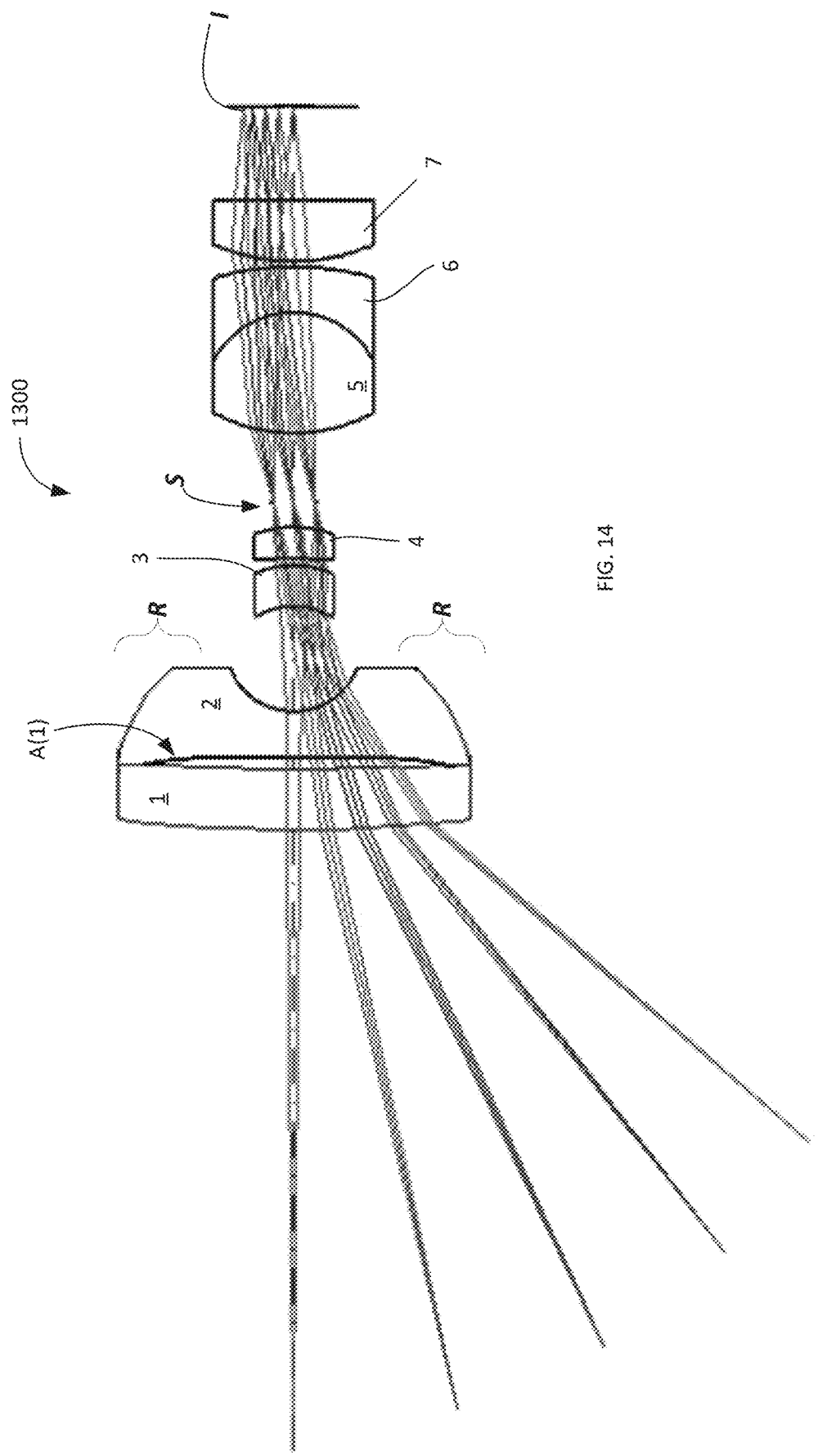
FIG. 14 is a schematic of FIG. 13 indicating the FFOV only.

An Embodiment of a Portion of the Lens System Configured to Image Object in the FFOV:

In reference to FIG. 14 and Table 2.1, the front optical lens element 1 is a meniscus, followed by the negative lens (element 2, possessing negative optical power). A certain pre-defined annular extent of an outer portion of the aspheric surface A(1) of the lens element 2 (which is the front surface of this lens element 2 facing the FFOV) is configured as a reflector (denoted as R). The latter feature is discussed in more detail in reference to FIG. 15 and associated imaging of the LFOV.

With Respect to Imaging of the Object Space in the FFOV:

The embodiment 1300 of the optical objective includes 7 (seven) lens elements (with the overall length from the first optical surface to the surface of the detector 1350 of about 12 mm) and defines the FFOV of about +/−50 degrees with the depth of field (DoF) between about 5 mm and about 100 mm, with the spatial resolution of imaging of an object in the FFOV or about 50 microns. The maximum diametrical extent of the lens system 1300 does not exceed 5.8 mm. Material for some lens elements (providing the well-corrected imaging within the spectral bandwidth from about 450 nm to about 650 nm) is chosen to be plastic. While the optical detector is configured to provide a full image height of 2.2 mm, the image of the object space in the FFOV is characterized by a 0.836 mm semidiameter. For the purposes of this design, the object space viewed in the FFOV was considered to be a spherical surface centered on the axis 1340 at located at the object distance of about 100 mm.

Figure 16A:
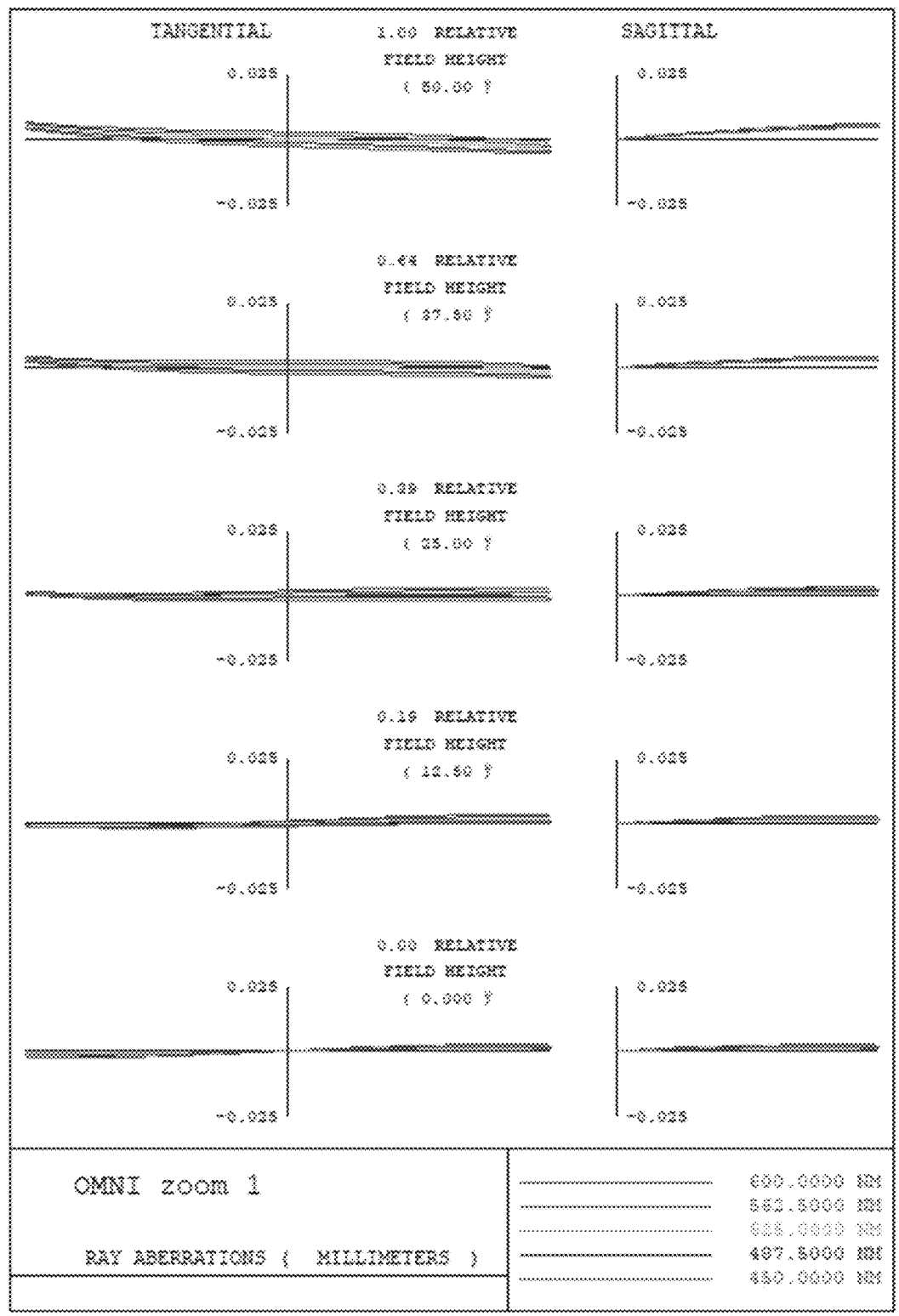
FIG. 16A provides description of transverse ray aberrations of the embodiment of FIG. 13 during the optical imaging in the FFOV only.
Figure 16B:
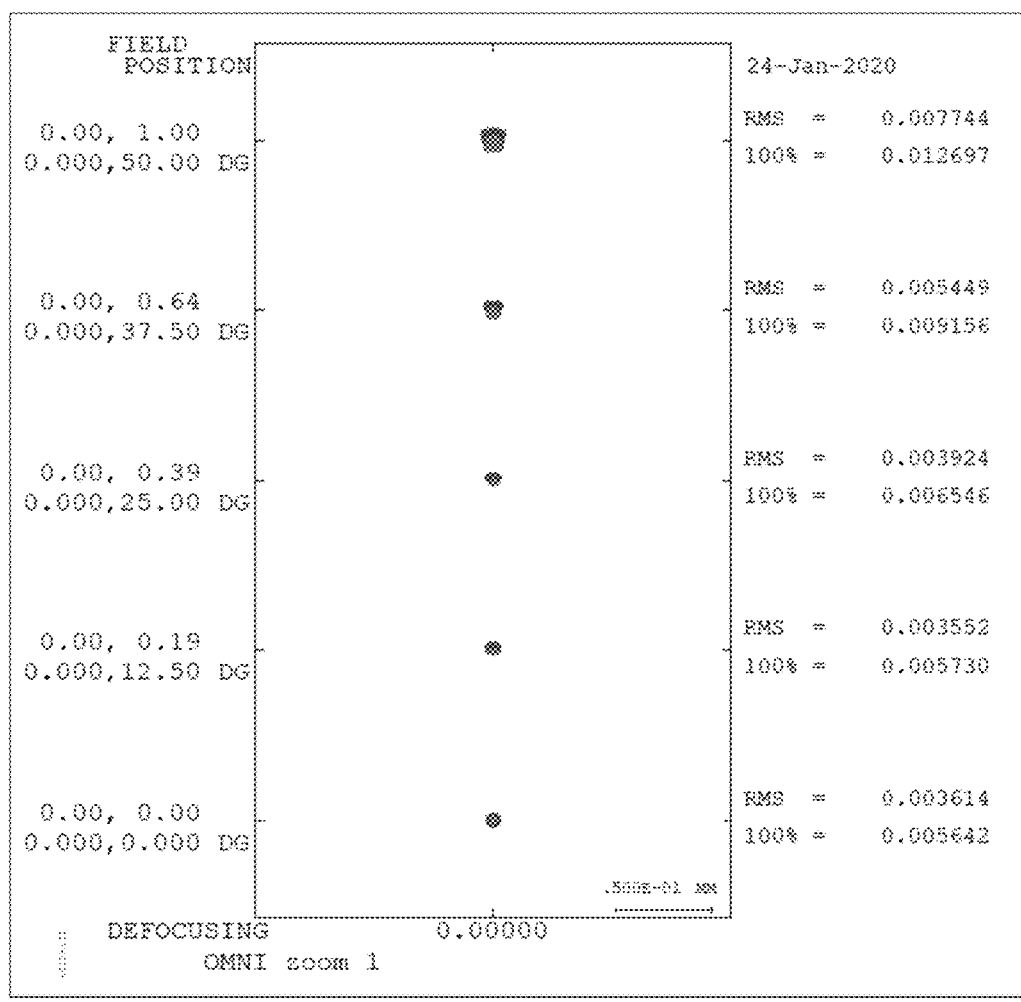
FIGS. 16B, 16C illustrate the spot diagrams, field curves, and distortion characteristics of the embodiment of FIG. 13 associated with imaging of the object space in the FFOV only.
Figure 16C:
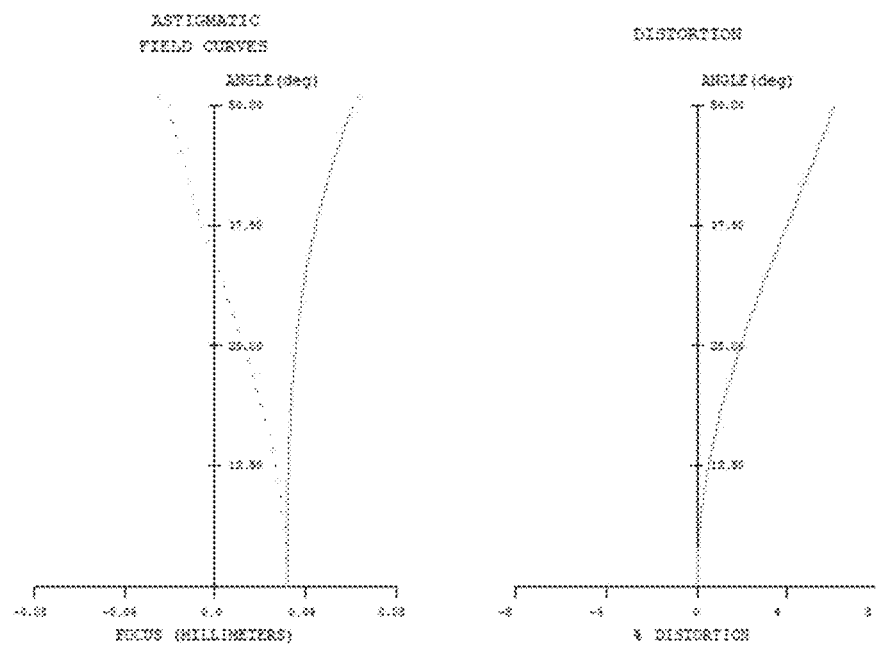

FIG. 16A illustrates transverse ray aberrations representing optical performance of the embodiment 1300 during the imaging in the FFOV: these aberrations are substantially below 25 microns for any field up to at least 50 microns. FIGS. 16B, 16C illustrate the corresponding spot diagrams and the field curvature and distortion as a function of field angle. The spot diagrams boast the rms spot size below about 7.7 microns at the full field height (field of 50 degrees) and below 3.6 microns for imaging the axial portion of the object in the FFOV. The distortion figure is notably within only 5% for field angles up to 40 degrees (FIG. 16C) which, in the case of distortion, substantially corresponds to the level considered in related art to be a very good solution (while practically-acceptable level of distortion, targeted by the related art, is about 5% as well).

Figure 17:
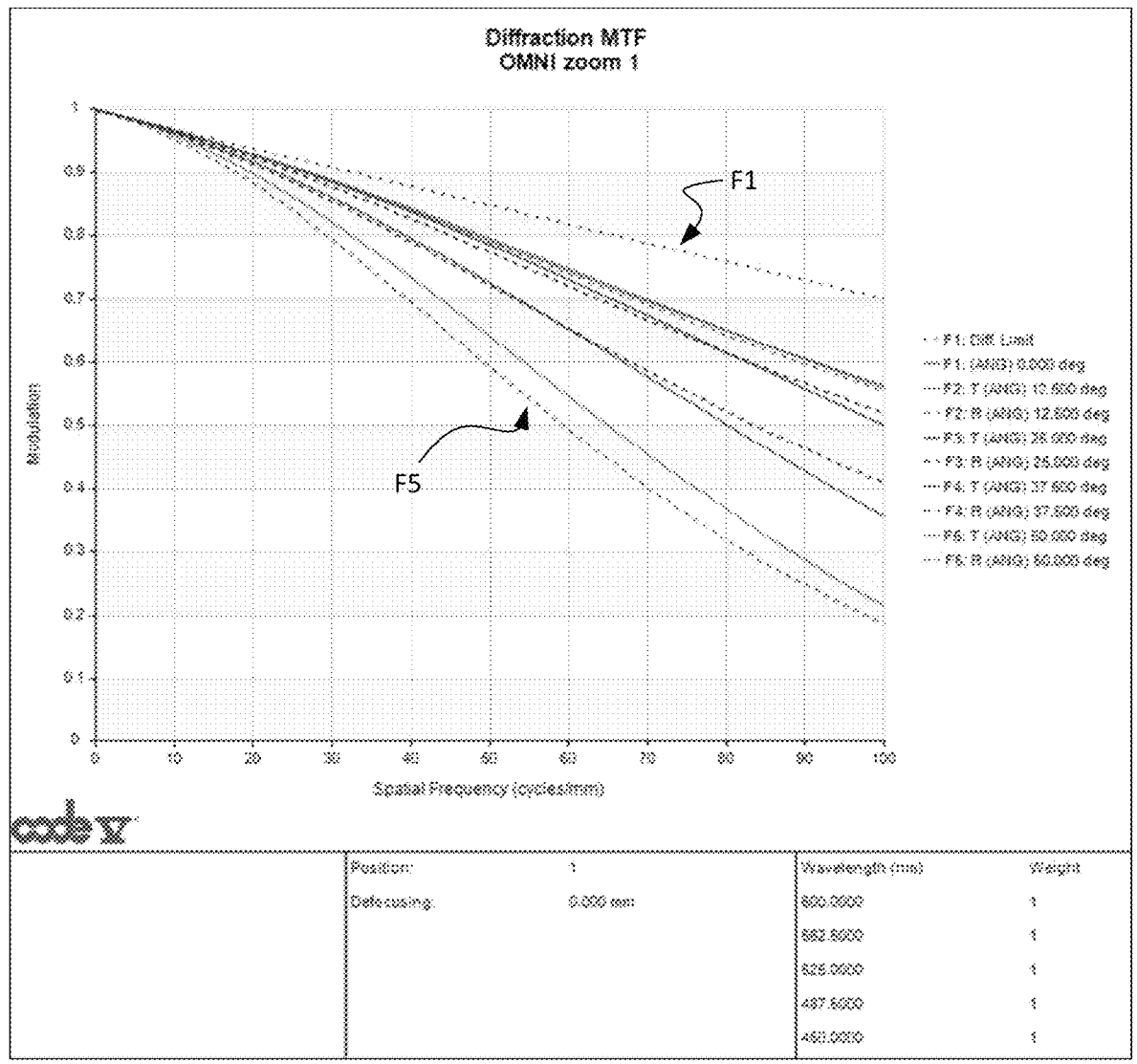
FIG. 17 presents the curves of the modulated transfer function (versus field) for the embodiment of FIG. 13 that characterizes the optical imaging in the FFOV only.

For assessing other types of aberrations, the identification of what is practically acceptable comes down to the modulated transfer function (MTF) curves. Based on the proposed design and in reference to FIG. 17 (that illustrates parameters of the MTF characterizing the operation of the embodiment 1300 in the visible portion of the spectrum in the FFOV), the ideal solution is substantially close to being diffraction-limited (the top curve among the MTF curves). Notably, the performance of the design on-axis is close to the ideal solution, with some falloff at the edge of the field—and would be considered practically acceptable by a person of ordinary skill in the art in visual and/or photographic optical systems. Specifically, the cut-off frequency of operation in the visible portion of the spectrum is always way above 100 cycles/mm (both for imaging in tangential and sagittal planes) and exceeding about 650 cycles/mm for imaging in the sagittal plane at any field angle up to at least 50 degrees.

Such consideration, accepted in related art, at least in part is explained by the specifics of the practical use of the system, where user generally positions the optical system such that the object of interest is in the center of the field. Based on the satisfying performance demonstrated by the MTF curves of FIG. 17, the proposed design is operationally sound at least in the visible portion of the optical spectrum.

Figure 15:
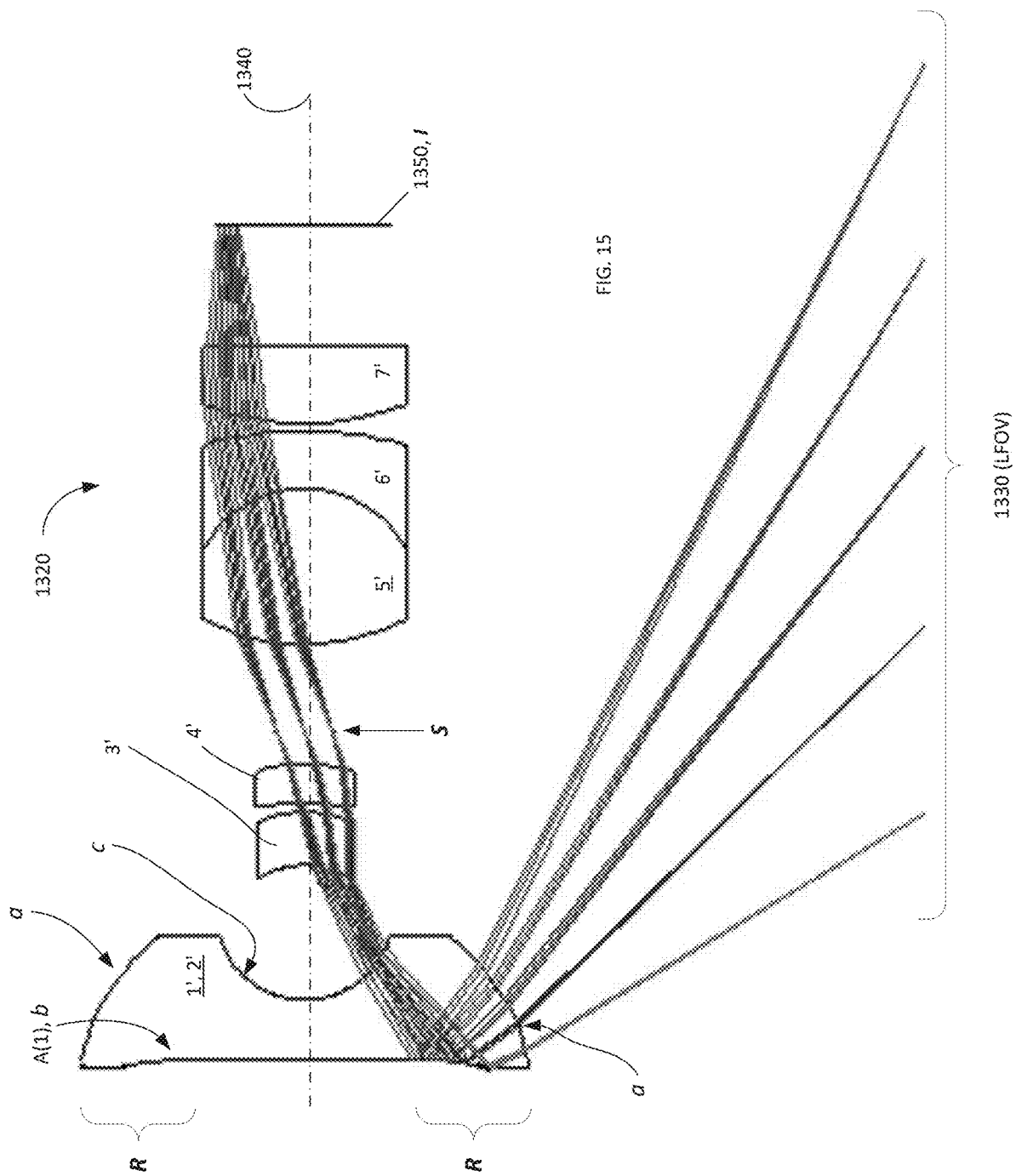
FIG. 15 is a schematic of a portion of the embodiment of FIG. 13 configured to image the object space in LFOV only.

A Portion of the Optical System Configured to Image Object in the LFOV:

Referring now to FIG. 15 and Table 2.2 (representing the description of the portion 1320 of the system 1300, configured to image, in operation, the object space in the LFOV as well), light is delivered from the object to the optical element (1',2')—which is the same as the lens element 2 of FIG. 14—at a range of viewing angles defining the LFOV 1330, collected through the side surface of this optical element (labelled "a"), and propagates through the body of the element (1', 2') towards the reflectively-coated annular portion R of the aspherical surface A(1) (which surface is also labelled as "b") to be reflected and then transmitted through the surface "c" upon its further propagation towards the portion of the lens that includes the sequence of the lens elements 3', 4', 5', 6', and 7'.

From comparing the data presented in Tables 1 and 2, a skilled artisan will readily appreciate that the second lens element of the overall system 1300 (denoted as 2 in Table 2.1) performs, in operation, the role of two optical elements (labelled 1', 2' in Table 2) for imaging of the LFOV because light from the LFOV propagates through this optic twice due to being reflected at the portion R of the aspherical surface A(1). For comparison purposes, the lens element 3' of Table 2.2 directly corresponds to the lens element 3 of Table 2.1, the lens element 4' of Table 2 directly corresponds to the lens element 4 of Table 1, the lens element 5' of Table 2 directly corresponds to the lens element 5 of Table 2.1, and so on. (Reversal of signs of curvature of some elements of Table 2.2 as compared to those of Table 2.1 represents, of course, the agreed upon and recognized in the related art convention of sign-reversal upon the reflection of light.)

With Respect to Imaging of the Object Space in the LFOV:

the portion of the detector configured as annulus with an inner semidiameter of about 0.836 mm and an outer semidiameter of about 1.1 mm is utilized, with the viewing angle (in substantially any plane containing the optical axis 1340) between 120-degrees and 155 degrees. (Accordingly, the circular image formed in the FFOV and the annular image formed in the LFOV are not spatially separated from one another in the plane of the detector: there lens system 1300 is designed to ensure that there is substantially no radial gap between these two images. For the purposes of this design, the object space viewed in the LFOV was considered to be a cylinder with a semidiameter of about 8 mm extending along and surrounding the axis 1340.

Figure 18A:
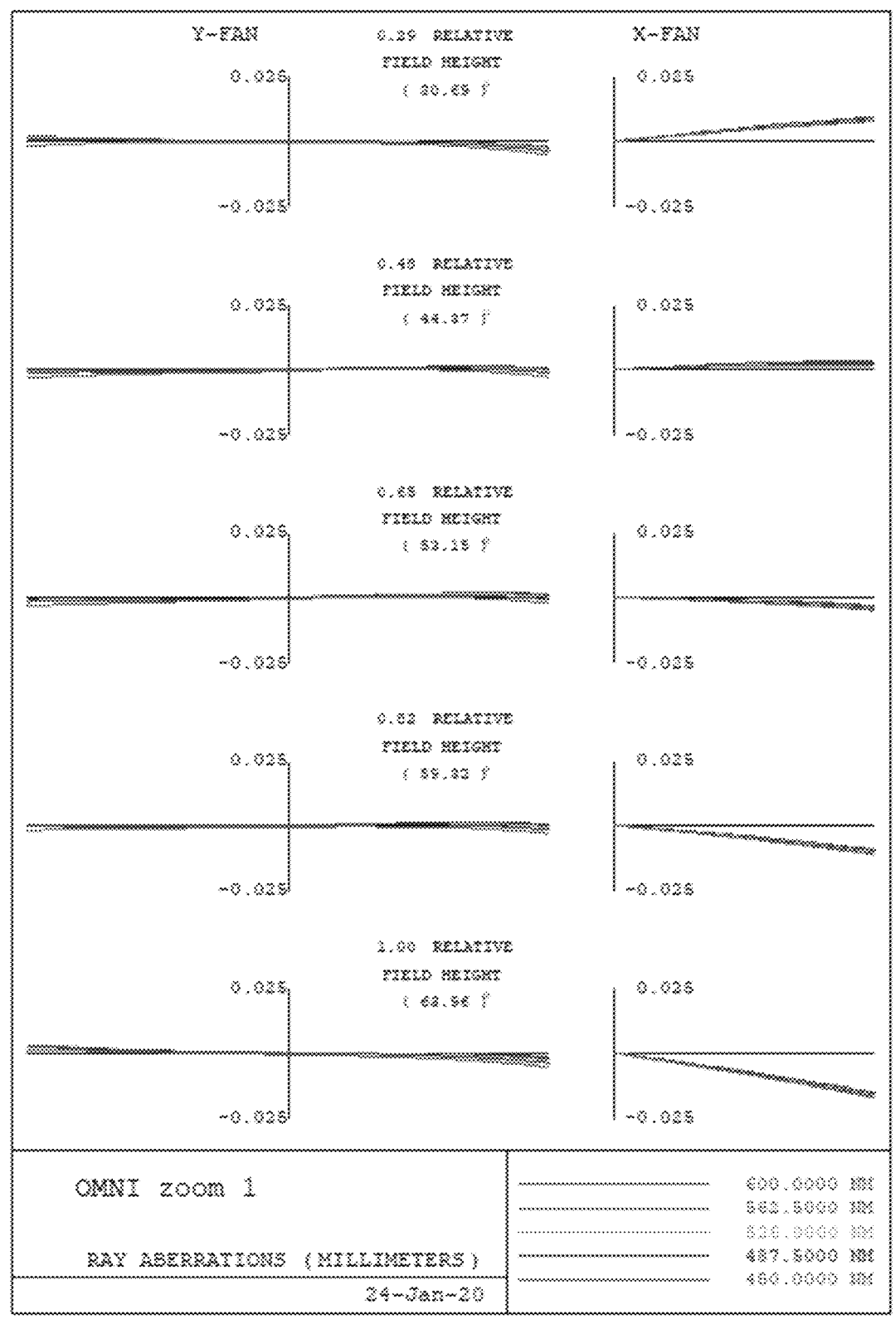
FIG. 18A provides description of transverse ray aberrations of the embodiment of FIG. 13 during the optical imaging in the LFOV only.

FIG. 18A illustrates transverse ray aberrations representing optical performance of the embodiment 1320 during the imaging in the LFOV: these aberrations are substantially below 25 microns for any field up to at least 50 microns. While the embodiment possesses some minimal residual astigmatism, it is well corrected for color aberrations. FIGS. 18B, 18C illustrate the corresponding spot diagrams and the field curvature as a function of field angle. The spot diagrams are presented for the fields between about 63.96 degrees (which corresponds to the viewing angle of about 114 degrees) and about 30.69 degrees (which corresponds to the viewing angle of about 120 degrees), thereby sufficiently covering the angular extent of the LFOV. The spot diagrams boast the rms spot size well below about 3.3 microns substantially for any field.

Figure 19:
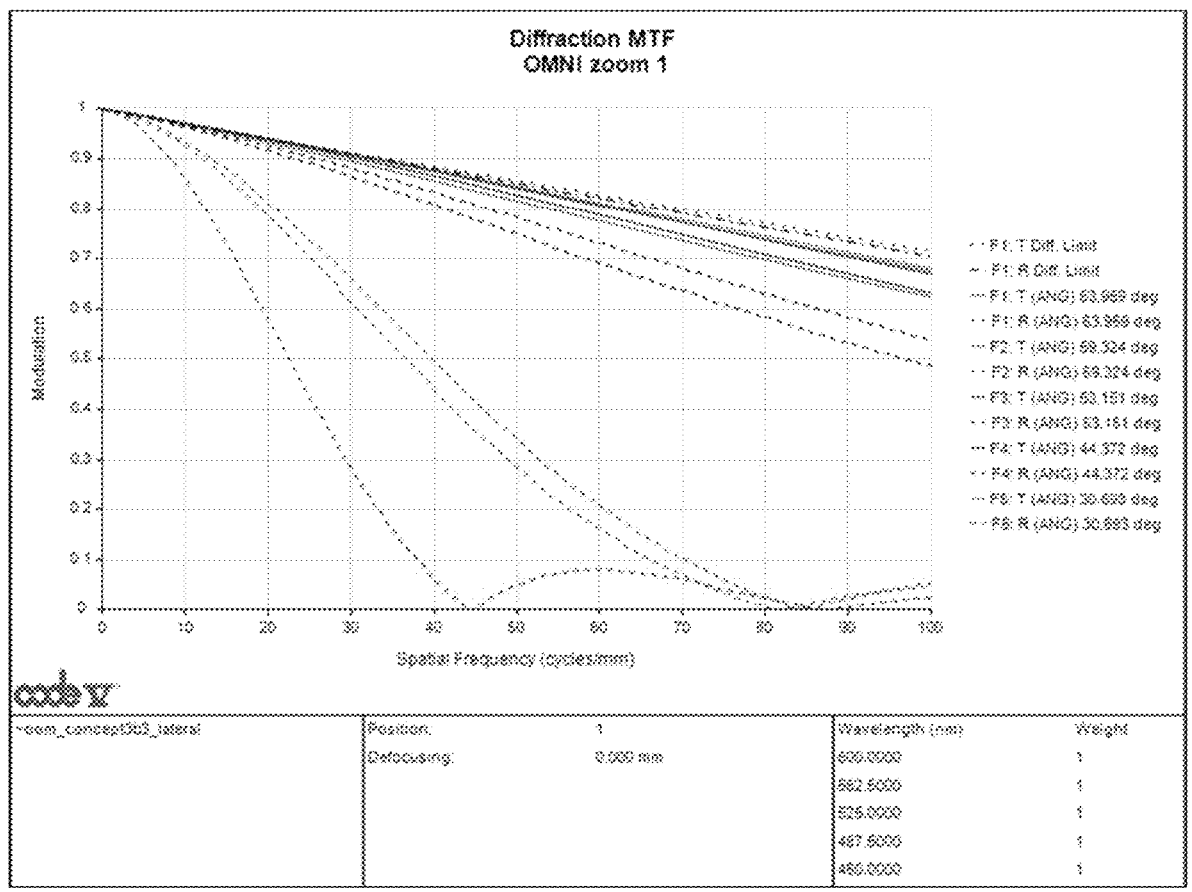
FIG. 19 presents the curves of the modulated transfer function (versus field) for the embodiment of FIG. 13 (or, its portion depicted in FIG. 15) that characterizes the optical imaging in the LFOV only.

Additional Aberrations can be Assessed from the MTF Curves of FIG. 19.

When used to image the object space marked with the pre-defined indicia of FIGS. 4A, 4B, the optical system 1300 forms combined, aggregate images that include the sub-images of the FFOV and the LFOV and that is substantially similar to the images presented in FIGS. 5A, 5B with the exception that the dark circle, separating the inner sub-image from the outer sub-image in each of FIGS. 5A, 5B, is not present due to the judicious configuration of the values of the FFOv and the LFOV, as was alluded to above. As acquired, the sub-image representing the object space in FFOV and that representing the object space in the LFOV are not co-directional, but then—according to the idea of the invention—are being transformed as discussed below to form a new image all portions of which are co-directional.

TABLE 2.1

| ELEMENT NUMBER | RADIUS OF CURVATURE | | THICKNESS | APERTURE DIAMETER | | MATERIAL |
|---|---|---|---|---|---|---|
| | FRONT | BACK | | FRONT | BACK | |
| OBJECT | 10.0000 | | 10.0000 | | 4.8562 | |
| | | 0.0000 | | | | |

TABLE 2.1-continued

| | | | | | | |
|---|---|---|---|---|---|---|
| 1 | 27.9499 CX | 44.0924 CC | 1.0000 | 5.6000 | 5.2000 | OKP4HT Osaka |
| | | | 0.2100 | | | |
| 2 | A (1) | 1.1324 CC | 0.7500 | 5.0000 | 2.0900 | E48R Zeon |
| | | | 1.7472 | | | |
| 3 | −1.1446 CC | −1.4965 CX | 0.6800 | 1.0772 | 1.0998 | E48R Zeon |
| | | | 0.1188 | | | |
| 4 | −4.1435 CC | −1.9743 CX | 0.5090 | 1.0238 | 0.9442 | E48R Zeon |
| | | | 0.4126 | | | |
| S (APERTURE STOP) | | | | | 0.6857 | |
| | | | 1.1455 | | | |
| 5 | 2.7743 CX | −1.4845 CX | 2.0000 | 1.4321 | 1.7216 | E48R Zeon |
| 6 | −1.4845 CC | −5.0127 CX | 0.7500 | 1.7216 | 1.9582 | OKP4HT Osaka |
| | | | 0.1000 | | | |
| 7 | 3.4701 CX | INF | 1.0000 | 2.0149 | 1.9250 | E48R Zeon |
| IMAGE DISTANCE = | | | 1.5767 | | | |
| I (IMAGE) | | INF | | | 1.6864 | |

NOTES
Positive radius indicates the center of curvature is to the right
Negative radius indicates the center of curvature is to the left
Dimensions are given in millimeters
Thickness is axial distance to next surface
Image diameter shown above is a paraxial value, It is not a ray traced value
Other glass suppliers can be used if their materials are functionally equivalent to the extent needed by the design; contact the designer for approval of substitutions.

ASHPERIC CONSTANTS $$Z = \frac{(CURV)Y^2}{1 + (1 - (1+K)(CURV)^2 Y^2)^{1/2}} + (A)Y^4 + (B)Y^6 + (C)Y^8 + (D)Y^{10}$$

| ASPHERIC | CURV | K | A | B | C | D |
|---|---|---|---|---|---|---|
| A (1) | 0.365808E−02 | 0.00000000 | −3.69341E−03 | 0.00000E+00 | 0.00000E+00 | 0.0000E+00 |

REFERENCE WAVELENGTH = 525.0 NM
SPECTRAL REGION = 450.0-600.0 NM

INFINITE CONJUGATES

| | |
|---|---|
| EFL = | 1.1583 |
| BFL = | 1.5014 |
| FFL = | 2.5045 |
| F/NO = | 4.4691 |

AT USED CONJUGATES

| | |
|---|---|
| REDUCTION = | 0.0926 |
| FINITE F/NO = | 4.5000 |
| OBJECT DIST = | 10.0000 |
| TOTAL TRACK = | 22.0000 |
| IMAGE DIST = | 1.5767 |
| OAL = | 10.4233 |

PARAXIAL

| | |
|---|---|
| IMAGE HT = | 0.7912 |
| IMAGE DIST = | 1.6087 |

SEMI-FIELD

| | |
|---|---|
| ANGLE = | 50.0000 |

ENTR PUPIL

| | |
|---|---|
| DIAMETER = | 0.2592 |
| DISTANCE = | 2.5903 |

EXIT PUPIL

| | |
|---|---|
| DIAMETER = | 3.4975 |
| DISTANCE = | −14.1293 |

NOTES
FFL is measured from the first surface
BFL is measured from the last surface

TABLE 2.2

| ELEMENT NUMBER | RADIUS OF CURVATURE FRONT | RADIUS OF CURVATURE BACK | THICKNESS | APERTURE DIAMETER FRONT | APERTURE DIAMETER BACK | MATERIAL |
|---|---|---|---|---|---|---|
| OBJECT | INF | | 8.0000 | | | |
| | DECENTER(1) | | | | | |
| | | | | 10.0840 | | |
| | | | 0.0000 | | | |
| | | | | 9.5983 | | |
| | | | −1.0000 | | | |
| 1' (a, b) | 2.9775 CX | A(1) | 2.2500 | 5.7257 | 4.8568 | E48R Zeon |
| | A(1) | | | | 4.8568 | REFL |
| 2' (b, c) | A(1) | −1.1324 CC | −0.7500 | 4.8568 | 4.8568 | E48R Zeon |
| | | | −1.7472 | | | |
| 3' (= 3) | 1.1446 CX | 1.4965 CX | −0.6800 | 1.2918 | 1.2961 | E48R Zeon |
| | | | −0.1188 | | | |
| 4' (= 4) | 4.1435 CC | 1.9743 CX | −0.5090 | 1.1698 | 1.0500 | E48R Zeon |
| | | | −0.4126 | | | |
| S (APERTURE STOP) | | | | 0.6857 | | |
| | | | −1.1455 | | | |
| 5' (= 5) | −2.7743 CX | 1.4845 CX | −2.0000 | 1.7684 | 2.1112 | E48R Zeon |
| 6' (= 6) | 1.4845 CC | 5.0127 CX | −0.7500 | 2.1112 | 2.4709 | OKP4HT Osaka |
| | | | −0.1000 | | | |
| 7' (= 7) | −3.4701 CX | INF | −1.0000 | 2.5951 | 2.5016 | E48R Zeon |
| IMAGE DISTANCE | | | −1.5767 | | | |
| I (IMAGE) | | INF | | 2.2075 | | |

NOTES
Positive radius indicates the center of curvature is to the right
Negative radius indicates the center of curvature is to the left
Dimensions are given in millimeters
Thickness is axial distance to next surface
Image diameter shown above is a paraxial value, it is not a ray traced value
Other glass suppliers can be used if their materials are functionally equivalent to the extent needed by the design; contact the designer for approval of substitutions.

ASHPERIC CONSTANTS $$Z = \frac{(CURV)Y^2}{1 + (1 - (1 + K)(CURV)^2 Y^2)^{1/2}} + (A)Y^4 + (B)Y^6 + (C)Y^8 + (D)Y^{10}$$

| ASPHERIC | CURV | K | A | B | C | D |
|---|---|---|---|---|---|---|
| A (1) | −0.365808E−02 | 0.00000000 | 3.69341E−03 | 0.00000E+00 | 0.00000E+00 | 0.0000E+00 |

DECENTERING CONSTANTS

| DECENTER | X | Y | Z | ALPHA | BETA | GAMMA |
|---|---|---|---|---|---|---|
| D (1) (REVE) | 0.0000 | 0.0000 | 0.0000 | −90.0000 | 0.0000 | 0.0000 |

A decenter defines a new coordinate system (displaced and/or rotated) in which subsequent surfaces are defined. Surfaces following a decenter are aligned on the local mechanical axis (z-axis) of the new coordinate system. The new mechanical axis remains in use until changed by another decenter. The order in which displacements and tilts are applied on a given surface is specified using different decenter types and these generate different new coordinate systems; those used here are explained below. Alpha, beta, and gamma are in degrees.

DECENTERING CONSTANT KEY:

| TYPE | TRAILING CODE | ORDER OF APPLICATION |
|---|---|---|
| DECENTER | | DISPLACE (X, Y, Z) |
| | | TILT (ALPHA, BETA, GAMMA) |
| | | REFRACT AT SURFACE |
| | | THICKNESS TO NEXT SURFACE |
| REVERSE DECENTER | REVE | REFRACT AT SURFACE |
| | | TILT (−GAMMA, −BETA, −ALPHA) |
| | | DISPLACE (−Z, −Y, −X) |
| | | THICKNESS TO NEXT SURFACE |

REFERENCE WAVELENGTH = 525.0 NM
SPECTRAL REGION = 450.0-600.0 NM

This is a non-symmetric system. If elements with power are decentered or tilted or have user-defined or CAD surfaces, the first order properties as determined from the paraxial ray trace may be inaccurate. Use Tools > Macro Manager . . . Sample Macros > 1st Order Analysis > FirABCD to compute the 1st order parameters via an ABCD matrix method.

TABLE 2.2-continued

| INFINITE CONJUGATES | |
|---|---|
| EFL = | -2.5609 |
| BFL = | -0.9745 |
| FFL = | 5.9232 |
| F/NO = | 4.3630 |

| AT USED CONJUGATES | |
|---|---|
| REDUCTION = | 0.1839 |
| FINITE F/NO = | 4.5000 |
| OBJECT DIST = | 8.0000 |
| TOTAL TRACK = | -1.5400 |
| IMAGE DIST = | -1.5767 |
| OAL = | -7.9633 |
| PARAXIAL | |
| IMAGE HT = | 0.3525 |
| IMAGE DIST = | -1.4456 |
| SEMI-FIELD | |
| ANGLE = | 30.6930 |
| ENTR PUPIL | |
| DIAMETER = | 0.5870 |
| DISTANCE = | 6.3574 |
| EXIT PUPIL | |
| DIAMETER = | 3.4618 |
| DISTANCE = | 14.1293 |

NOTES
FFL is measured from the first surface
BFL is measured from the last surface Accordingly, upon the acquisition of the images of the FFOV and the LFOV with the lens system 1300, these images are not co-directional and have to be transformed to implement the idea of the invention and to make them co-oriented and co-directional.

Figure 13:
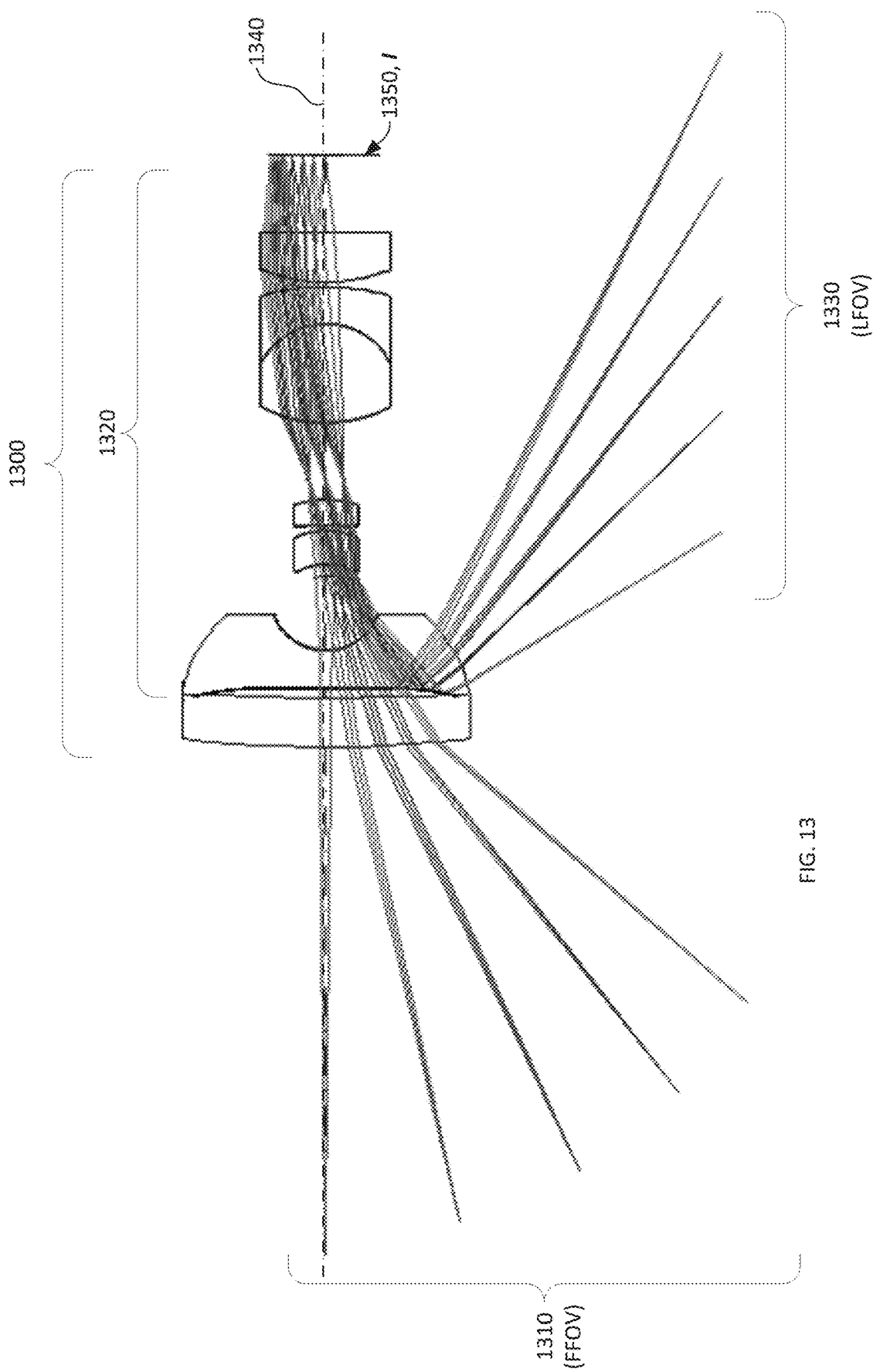
FIG. 13 presents an optical train of a lens structured conventionally (in a fashion similar to that of FIG. 1) and configured to acquired optical information from both the FFOV and the LFOV.

In one case, this transformation is achieved by forming a new image from the images produced by the lens system of FIG. 13 as a result of spatial redistribution of irradiance of these images.

Transformation of the Acquired Image: Irradiance-Redistribution Methodology

Figure 8:
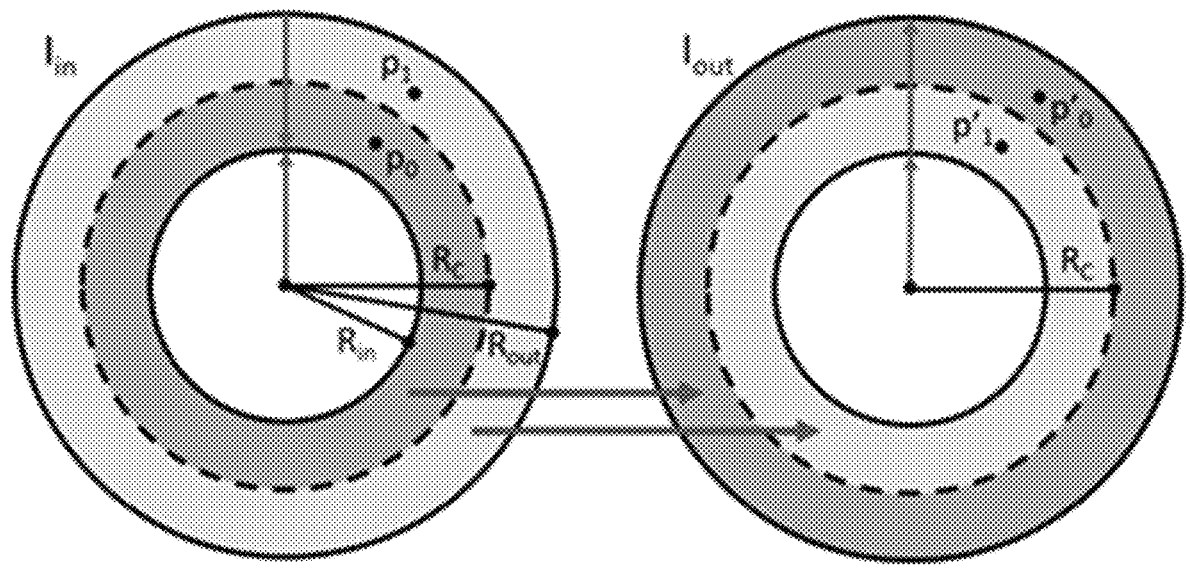
FIG. 8 provides illustrations to various definitions used in the image re-mapping process. Here, shaded areas are remapped from $I_{in}$ to $I_{out}$.

The idea behind the targeted spatial redistribution of irradiance of the initially not-co-directional images is based on reflecting upon itself the sub-image representing the object space in the LFOV across a circle with a chosen radius $R_C$. In reference to the schematic of FIG. 8, the LFOV image is in the area (portion of the aggregate image) defined in the image plane between the radius $R_{in}$ (providing a "seam" between the LFOV and FFOV views in the image plane) and the radius $R_{out}$, which is the outer limit of the LFOV view. $R_C$ is judiciously selected based on R and $R_{out}$, in a form containing and arithmetic mean and/or geometric mean of $R_{in}$ and $R_{out}$.

$$R_C = \frac{R_{in} + R_{out}}{2} \quad (1)$$

$$R_C = \sqrt{R_{in} R_{out}} \quad (2)$$

In the spatially-continuous domain, the image transformation can be defined by a remapping function $f(r)$ configured to transform the value of the radius $r_0$ of a point $p_0=(r_0; \theta)$ in the LFOV portion of the image by reflecting the point $p_0$ across $R_C$ to define point $p_1$ with the radius $r_1$: $p_1=(r_1; \theta)$. Notably, the remapping does not change the angle $\theta$ of the point's polar coordinate representation. Given these requirements, two limiting remapping functions can be chosen:
the function $f_a(r)$ for the situation when $R_C$ is defined as the arithmetic mean of the rear radii (see Eq 1); or
the function $f_g(r)$ for the situation when $R_C$ is defined as the geometric mean of the rear radii (see Eq 2).

$$f_a(r)=2R_C-r \quad (3)$$

$$f_g(r)=R_C^2/r \quad (4)$$

As intended, for each of these functions $f_a$, $f_g$ no remapping of the irradiance distribution of the image occurs when $r=R_C$:

$$f(R_C)=R_C \quad (5)$$

Considering the fact that a given image formed by the optical system is represented by a pixelated distribution of optical radiation (due to the pixelated nature of a typical optical detector receiving the light delivered by the optical imaging system), an embodiment of the image-transformation procedure of the invention provides the methodology of conversion of irradiance distribution between the spatially-discrete and spatially-continuous domains.

The transformation of the discrete domain to the continuous domain is performed as follows. In further reference to FIG. 8—the input image portion and the output image portion $I_{out}$ are each represented by two-dimensional arrays of pixels, with number of rows and columns $n_{row}$ and $n_{col}$. A pixel P has a row and column ($P_{col}$, $P_{row}$). Each pixel P in either of these images can be converted into a point p in the continuous domain with the following equation:

$$p=(x_p,y_p)=(P_{col}-n_{col}/2+\tfrac{1}{2}, P_{row}-n_{row}/2+\tfrac{1}{2}) \quad (6)$$

The "½" terms in Eq. 6 perform the task of "moving" the pixel to the center of the square it defines. Regardless of which of major colors (R, G, B) a given pixel represents, such square is defined as having a side length of 1, which identifies the coordinates ($P_{col}$, $P_{row}$) with the upper left corner of the square associated with P. (Here, the direction of the y-axis is defined a pointing down, which is a standard notation in image representation in software). Adding ½ makes the point associated with this pixel in the center of the pixel's square. Additionally, t half the number of columns/rows is subtracted to move the origin of the point to the center of the image. As a result, the use of polar coordinates of the points can be made as their center shares the center of radii $R_C$, $R_{in}$, and $R_{out}$.

Once a given pixel of an image is converted to spatially-continuous domain, the polar coordinates of the point p, ($r_p$, $\theta_p$), are found. Then, point $p'=(f(r_p), \theta)$ is defined, which is point p remapped in the continuous domain as discussed above. Using the so-defined image point p', color values P of this image point are determined with the use of interpolation procedure. The interpolation procedure involves first converting p' to a point $p_1'$ in the discrete image domain by using the inverted form of Eq 6:

$$p_1' = (x_{p'}, y_{p'}) = (x_{p'} + n_{col}/2 - \tfrac{1}{2}, y_{p'} + n_{row}/2 - \tfrac{1}{2}) \quad (7)$$

Interpolation takes the point $p'_1$ on the image and selects color values for it based on that image based on, for example, linear interpolation between nearest neighbors.

Irradiance-redistribution may be carried out starting with the output pixels of the acquired image, due to the reflective nature of the remapping functions that provide unique one-to-one correspondence between the pixels of the initial and transformed images regardless of whether the arithmetic or geometric remapping function is chosen $f(r_0) = r_1 \Rightarrow f(r_1) = r_0$. For an output (transformed) image $I_{out}$ of the object space seen in the LFOV, each pixel P in the image with an associated continuous domain point p in the rear view is assigned color and/or irradiance values by finding $p'_1$ associated with p, then irradiance values are interpolated from the input (initial) image $I_{in}$. For pixels with p that are not present in the LFOV, the color/irradiance values associated with the pixel are simply copied from the corresponding pixels having the same spatial coordinates in the initial image $I_{in}$. The $p'_1$ associated with each pixel P can be calculated once each time $R_{in}$ or $R_{out}$ is redefined and later use as reference data.

Figure 9:
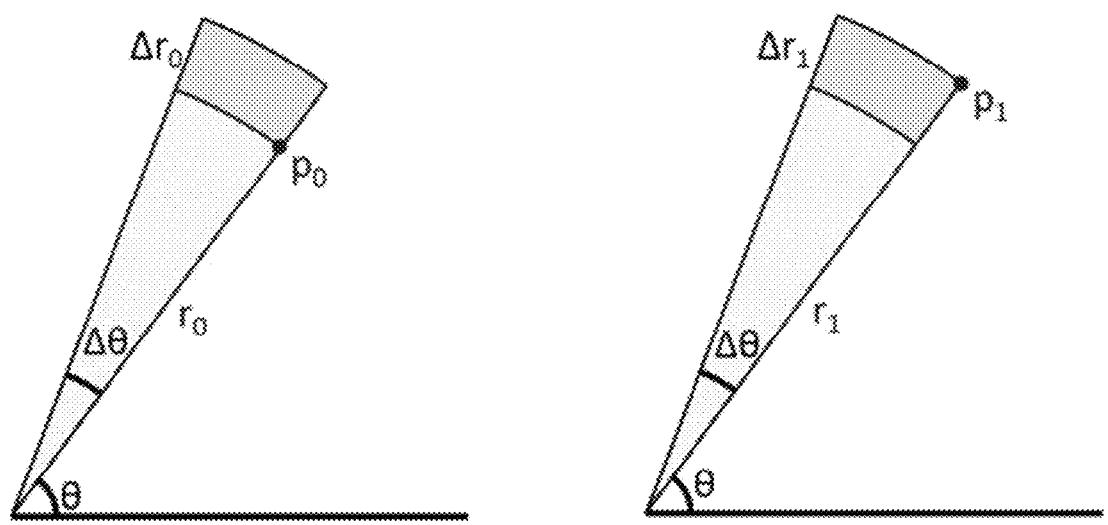
FIG. 9 schematically illustrates shapes used to define Aspect Ratio Preservation during the geometric mapping of the points of the conventional (not co-oriented and not co-directional) images formed with the use of a conventional optical imaging system to the points of the re-mapped (co-directional and co-oriented) images.

A person of skill in the art will readily appreciate that re-distribution of irradiance used to transform the optically-acquired image to change its directionality requires preserving the aspect ratio of a given pixel of the image upon such transformation 9 as the radial coordinate of the pixel if being changed). FIGS. 9A, 9B schematically illustrate spatial geometrical parameters used to define Aspect Ratio Preservation during the geometric mapping of the points of the conventional (not co-oriented and not co-directional) images formed with the use of a conventional optical imaging system to the points of the re-mapped (co-directional and co-oriented) images.

As mentioned above, when selecting a particular remapping function, one can choose $f_a(r)$ of (Eq 3) to ensure the radius of reflection $R_C$ is halfway between $R_{in}$, and $R_{out}$. Or one can choose $f_g(r)$ of (Eq 4), to maintain the aspect ratio of dimensions of corresponding pixels of the initial image and the transformed image. In a related embodiment, a remapping function can combine both $f_a(r)$ and $f_g(r)$ with appropriate weights.

For a given point $p_0 = (r_0, \theta)$ in the LFOV view, the first shape is defined as the space bounded between the radii of $r_0$ to $r_0 + \Delta r_0$ and the angular sector from $\theta$ to $\theta + \Delta\theta$. See FIG. 9A. Similarly, for a transformed point $p_1 = (f(r_0), \theta)$, the second shape is defined by the space bound between radii $r_1$ and $r_1 - \Delta r_1$ and the angular sector $\theta$ to $\theta + \Delta\theta$. See FIG. 9B. (Note that $\Delta r_1$ is subtracted due to the reflection of the image, which inverts the sign of $\Delta r_1$). Two ratios relating these first and second shapes are: the ratio of heights $H(r_0)$ and the ratio of widths $W(r_0)$, as defined in Eqs. (8) and (9), written for small angle approximations to convert circle section length to chord length and by letting $\Delta r_0$ approach zero.

$$H(r_0) = -\Delta r_1/\Delta r_0 = df(r_0)dr_0 = -f'(r_0) \quad (8)$$

$$W(r_0) = r_1 \Delta\theta / r_0 \Delta\theta = f(r_0)/r_0 \quad (9)$$

To prevent image distortion, H(r) and W(r) are chosen to be defined in the same fashion, so that any increase in height ratio is similarly found in an increase in width ratio. Setting these two equal preserves the aspect ratio through the reflection.

$$H(r) = W(r) \text{ and } -f'(r) = f(r)/f \quad (10)$$

It can be seen that $f_g(r)$ from Eq 4 is a solution to the differential equation Eq 10, which means it will preserve aspect ratio.

Weighting Functions

Figure 10:
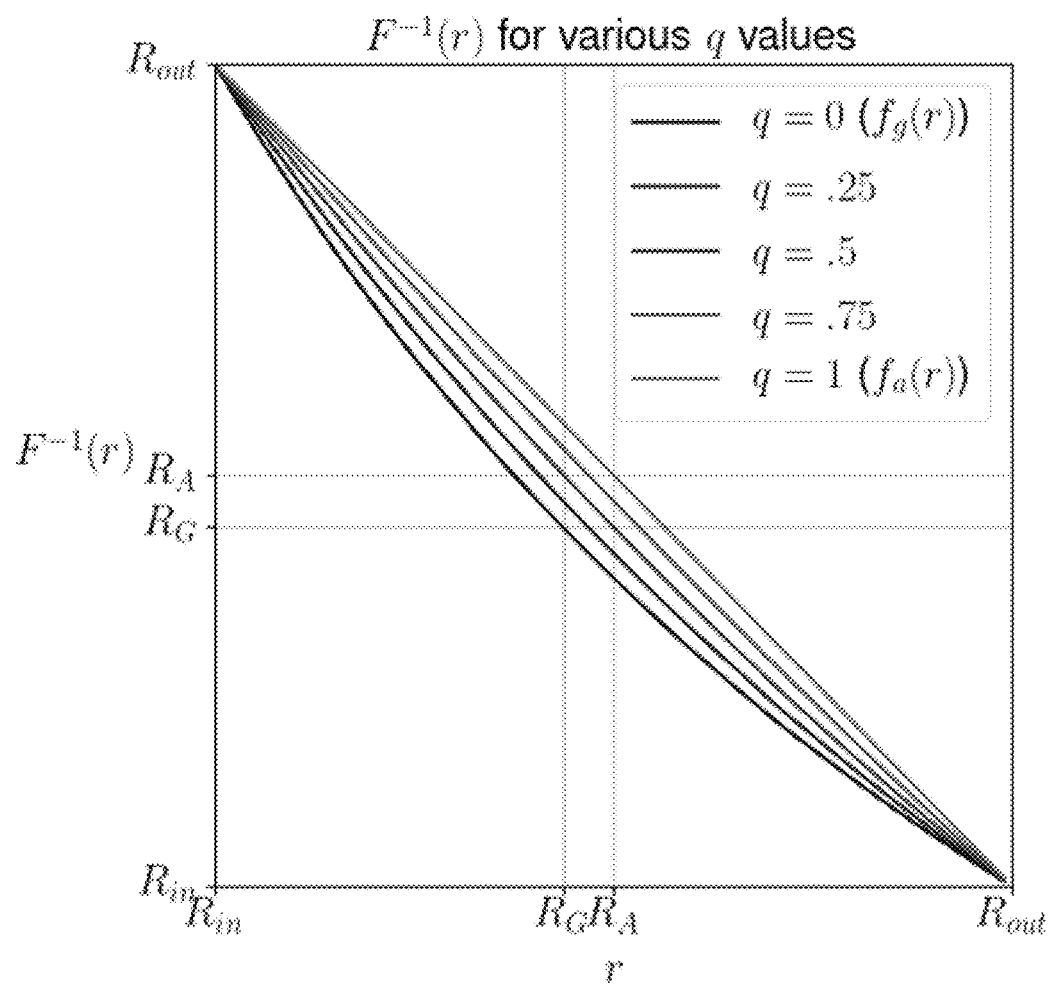
FIG. 10 contains plots illustrating inverse mapping for various values of the input parameter q.

The use of arithmetic and geometric remapping functions, $f_a(r)$ and $f_g(r)$, for spatial redistribution of the image irradiance may have very different effects on usability of an output (transformed) image. FIG. 10 contains plots illustrating inverse mapping for various values of the input parameter q.

In order to find a compromise between the advantages of either function, a more general remapping function F(r) is formed with an input parameter q, which is a weighting value, where $0 \leq q \leq 1$ and $q' = 1 - q$:

$$\begin{cases} F(r) = q f_a(r) + q' f_q(r) \\ R_A = \dfrac{R_{in} + R_{out}}{2} \\ R_G = \sqrt{R_{in} R_{out}} \\ F(r) = q(2R_A - r) + (1 - q) R_G^2 / r \end{cases} \quad (11)$$

$$F^{-1}(r) = \dfrac{(2qR_A - r) + \sqrt{(2qR_A - r)^2 + 4q'qR_G^2}}{2q} \quad (12)$$

Note that $f_a(r)$ uses $R_C = R_A$ and $f_g(r)$ uses $R_C = R_G$. F(r) is not reflective like $f_a(r)$ and $f_g(r)$ so one has to find its inverse, $F^{-1}(r)$.

When using this inverse mapping, the user finds the input point associated with each output pixel. When q=0, $F(r) = f_g(r)$, and when q=1, $F(r) = f_a(r)$. Therefore, the weighting value of q can be changed, depending on the specific implementation of the irradiance-redistribution, between 0 and 1 to define a remapping function F(r) that works as a compromise between the arithmetic mean and geometric mean remapping functions.

The methodology of redistribution of irradiance of an image portion representing the object space observed in the LFOV with the purpose of forming a transformed image portion with reversed directionality can be summarized as follows:

1) Start with a blank output (transformed) image. The output (transformed) image is built one pixel at a time.
2) To determine the value for each pixel p in the output image:
a. Use p's column and row, ($p_{col}, p_{row}$), to find the pixel's position relative to the center of the output image: ($x_{out}, y_{out}$).
b. Convert this position to polar coordinates: ($r_{out}, \theta_{out}$).

c. Find the remapping source position for this pixel: $(r_{in}, \theta_{in}) = (f(r_{out}), \theta_{out})$.
d. Convert the source position to Cartesian coordinates relative to the origin of the image (origin is the top-left corner): $(x_{in}, y_{in})$.
e. Use bilinear interpolation to obtain a color value of the input image using the source position coordinates.
f. This takes a continuous position on an image, $(x_{in}, y_{in})$ {e.g. the position (4.326,2.195)} and finds the value it should be using a weighted average of the discrete pixels it is nearest to, {e.g. the pixels at coordinates (4,2), (4,3), (5,2), (5,3)}.
3) Set the value of each output image pixel using the above method. The values of pixels which aren't within the remapping range are simply copied from the input image (these pixels make up the front view).

Additionally, the following steps can be taken during the spatial re-distribution of the irradiance of the initial image to reduce redundancy of the procedure:

Upon any change to calibration settings that modify the remapping, construct a data structure M that maps a pixel p on the output image to a position on the input image using steps 2a-2d above: $M[P_{col}, P_{row}] = (x_{in}, y_{in})$.

Replace steps 2a-2d in the above process with the following:

Find $(x_{in}, y_{in})$ for p, by obtaining the position on the input image from the data structure: $M[P_{col}, P_{row}] = (x_{in}, y_{in})$.

Example 2.2 of an Optical System Used with an Embodiment of the Invention

According to the idea of an alternative embodiment of the invention, an optical imaging system configured for simultaneous imaging of the object space in the FFOV and the LFOV is structured to have two optical sensors (detectors), each forming an image of only one corresponding FOV from the LFOV and FFOV. The detector dedicated to imaging of the object in the FFOV is complemented with its own, respectively-corresponding optical sub-system that collects light only from the FFOV, while the detector dedicated to imaging of the object space in the LFOV is complemented with its own, respectively-corresponding optical sub-system configured to collect light only from the LFOV. According to the idea of the invention, these two optical sub-systems and the corresponding optical detectors are spatially-distinct from one another such that light acquired by the overall optical imaging system from the FFOV passes through optical elements that do not interact with light acquired by the overall system from the LFOV, and vice versa.

Figure 20A:
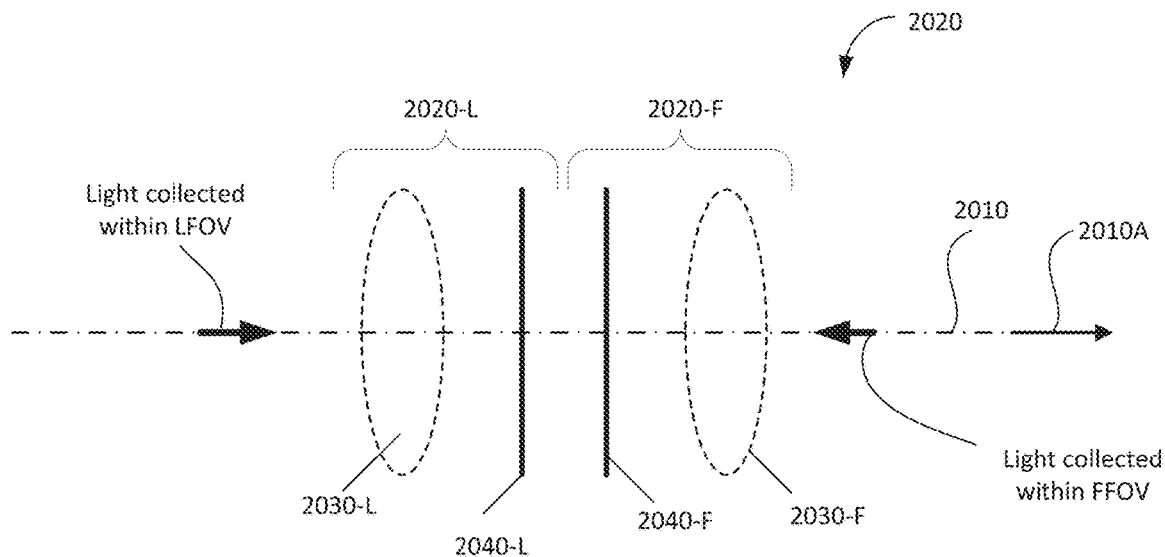
FIGS. 20A, 20B are schematic illustrations of related embodiments employing a multiple-sensor design of the optical imaging system, and configured to separate spatially light acquisition from the FFOV and the LFOV.
Figure 20B:
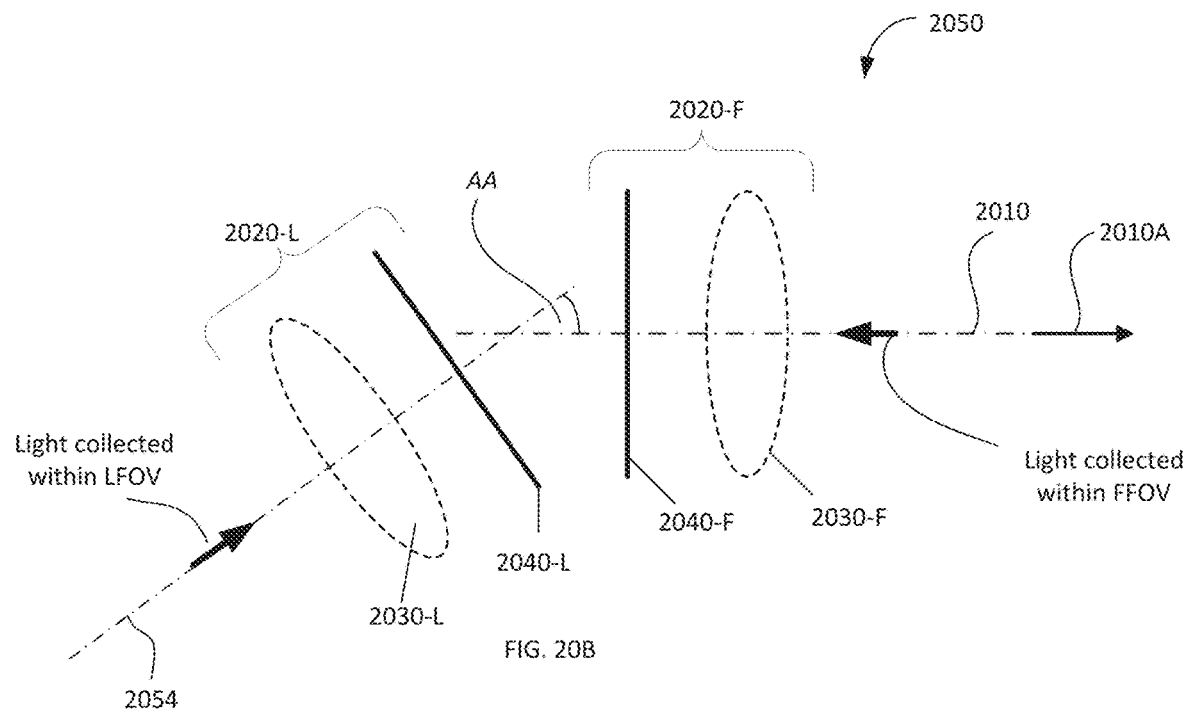

Schematic illustrations of two related implementations of this type are shown in FIGS. 20A, 20B. FIG. 20A, for example, illustrates the embodiment 2020 with the axis 2010 (a positive direction of which is denoted with the arrow 2010A). The two sub-systems 2020-F (configured to collect light from the FFOV of the system 2020) and 2020-L (configured to acquire light from the LFOV of the system 2020) are disposed co-axially, and each is formed by a corresponding lens (or lens system) and a corresponding optical detector: (2030-F, 2040-F) and (2030-L, 2040-L), accordingly. Each of lenses 2030-F, 2030-L are shown to be generalized, in dashed lines, and may include one or more lenslets of lens elements. FIG. 20B contemplates a related structure in 2050 which the rear portion 2020-L of the imaging system and the front portion 2020-F of the imaging system are not co-axial: the respectively-corresponding axes 2054 and 2010 are inclined at an angle AA.

A skilled artisan will readily appreciate that, generally, the sub-systems 2020-L and 2020-F may be structured to possess different optical and/or geometrical characteristics, and, depending on the goals of the particular design, provide different spatial resolution, different lateral magnification, etc. Therefore, details of different designs for sub-systems 2020-F, 2020-L are not discussed here in any further details. However, one non-limiting example of the system 2020, in which the optical sub-systems are substantially identical, are provided in reference to FIGS. 21, 22, 23A, 23B, and 24.

Description of Embodiment of the Lens 2120-L

Several notes are in order concerning a related embodiment of the utilized lens system.

Figure 21:
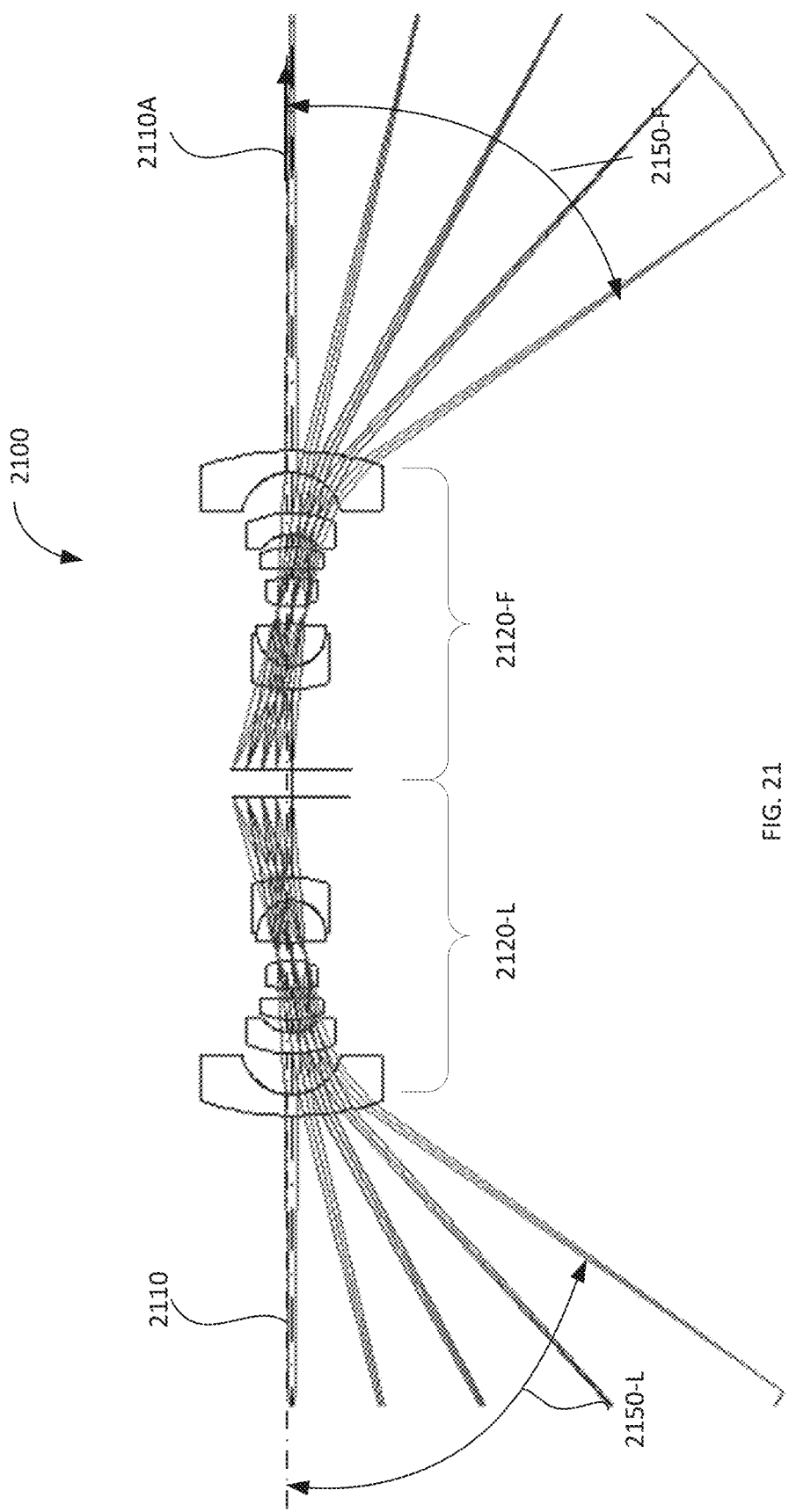
FIG. 21 presents an optical train of a specific embodiment of the multiple-sensor optical imaging system of FIG. 20A.
Figure 22:
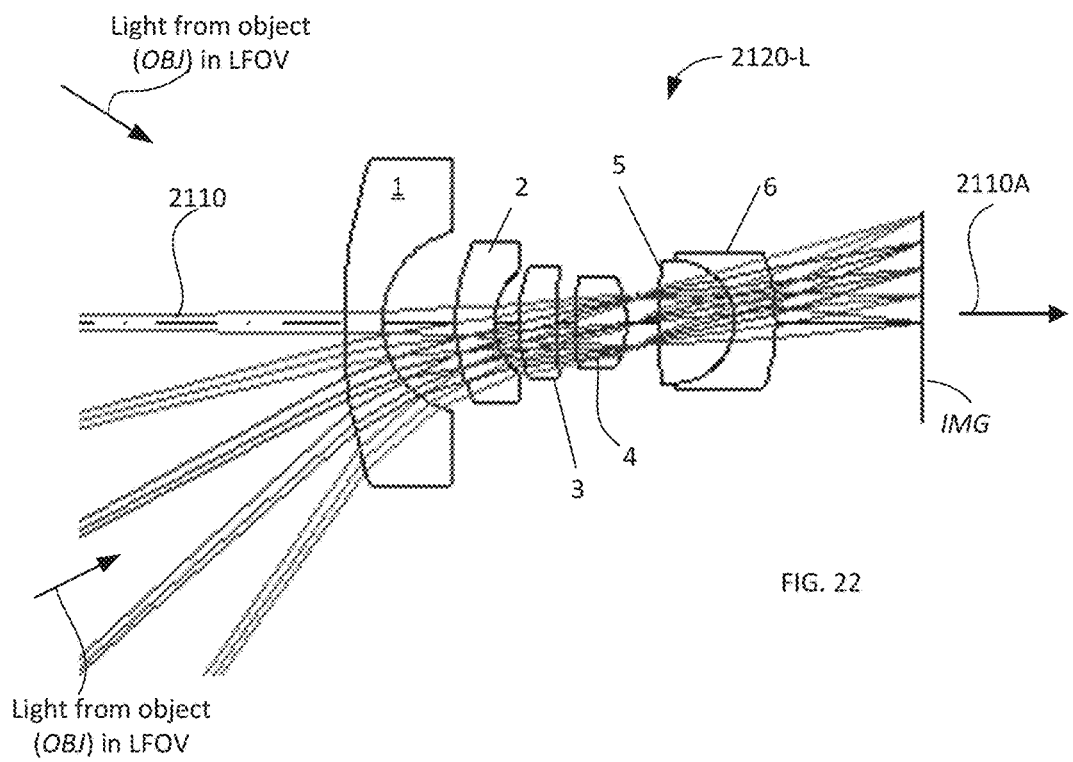
FIG. 22 illustrates a portion of the embodiment of FIG. 21 structured to collect light from the LFOV of the system of FIG. 21.
Figure 23A:
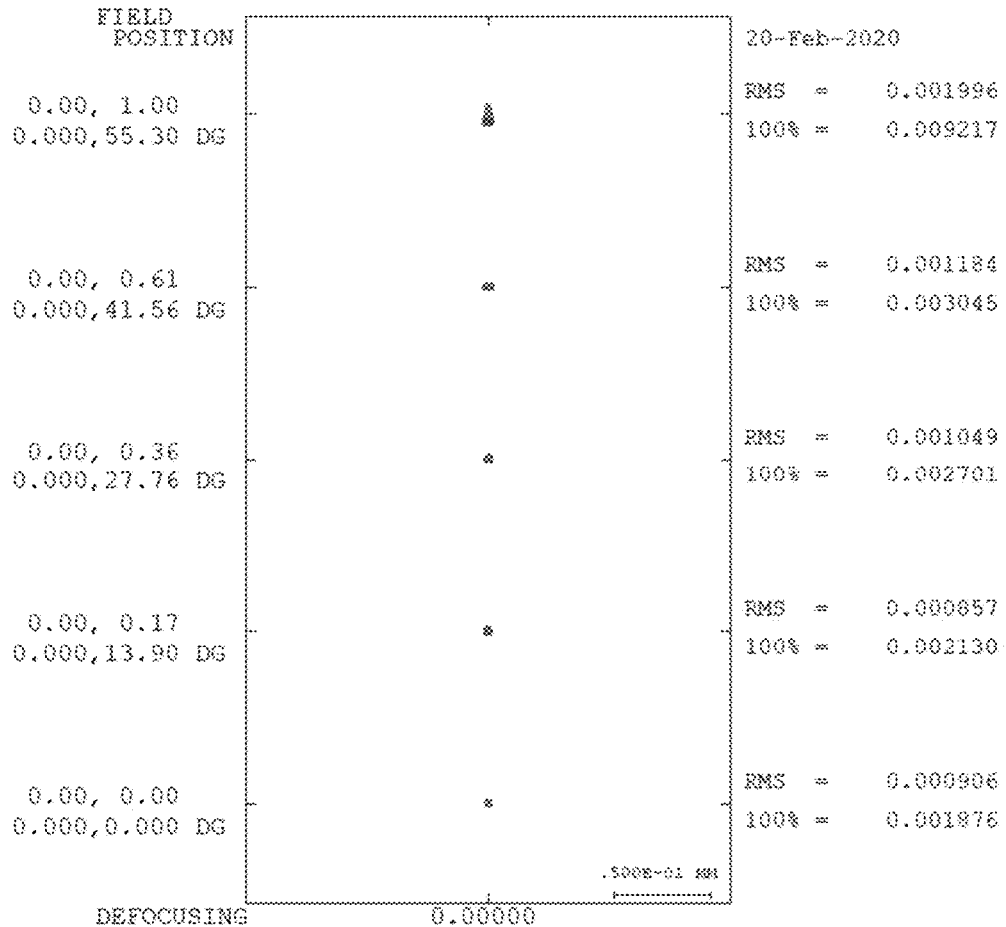
FIGS. 23A and 23B depict spot diagrams and ray aberration characteristics associated with operation of the embodiment of FIG. 22.
Figure 23B:
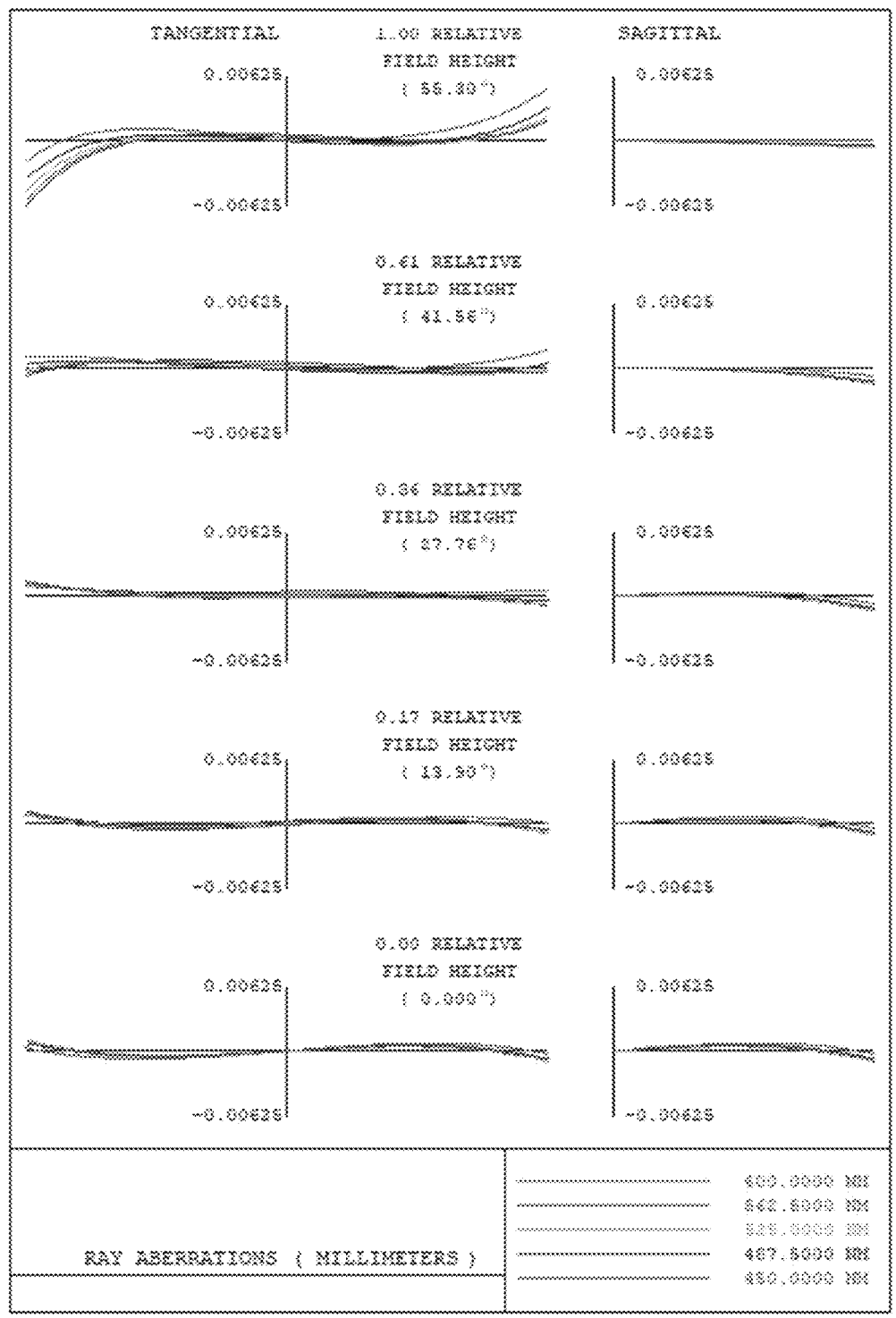
Figure 24:
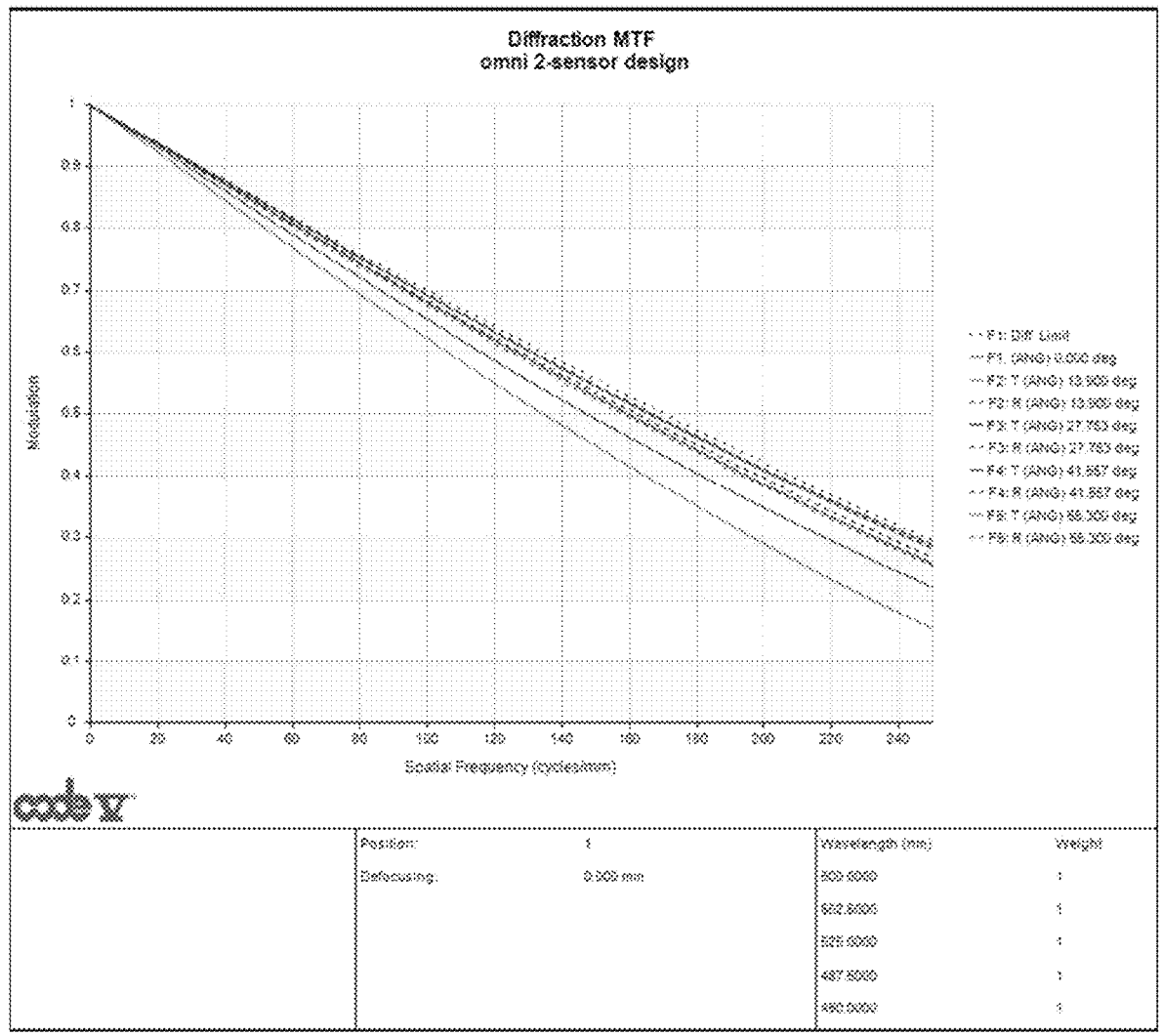
FIG. 24 presents the curves of the modulated transfer function (versus field) for the embodiment of FIG. 22 that characterizes the formation of optical image with either portion 2120-L or portion 2120-F of the system of FIG. 21.

Embodiment 2100 of FIG. 21 contains two substantially-identical optical imaging systems 2120-L and 2120-F, which are characterized by the LFOV and the FFOV (half-angles 2150-L and 21-50-F of which are shown), respectively. Table 2.3 summarizes data representing an optical train (sequence) 2120-L (FIG. 22) that is a portion of the lens system 2100 1 and that is used for imaging of the ambient space in the LFOV. It is understood that, because the specific example of the embodiment 2100 is substantially spatially-symmetric—that is, the optical structures 2120-F and 2120-L are substantially identical—the opto-geometrical design of the 2120-F portion of the system 2100 of FIG. 21 is the same as that of the 2120-L portion. The optical axis is denoted as 2110, and the arrow 2110A indicates the positive direction of the optical axis 2110 (which defines the viewing angles at which the object in the LFOV is observed by the system 2120-L.

The design prescriptions for the embodiments were generated with Code V and are discussed in reference to corresponding figures. In Table 2.3, optical elements and, possibly, media separating some of the elements, are numbered in a "backward" fashion, starting from that which is the closest to the object/target plane towards the plane of the optical sensor of the embodiment. Such approach to numbering of the optical elements makes it easier, as would be appreciated by a skilled artisan, to define the numerical aperture (NA) during the process of optical design. For example, the closest to the FFOV ambient space object lens element is labeled as element 1 both in Table 2.1 and FIG. 14; the next lens elements is element 2, and so on, while the plane of the optical sensor is referred to as an image plane and labeled as "I". Positive radius value for a given surface indicates that the center of curvature of such surface is to the right of the surface, while a negative radius value indicates that the center of curvature is to the left of the surface; dimensions are provided in millimeters; thickness is defined as an axial distance from a given surface to the next surface; and an indicated image diameter is a paraxial value and not a ray-traced value. Furthermore, with respect to decentering constants (if any), a decenter defines a new coordinate system (displaced and/or rotated) in which subsequent surfaces are defined. In such a case, surfaces following a decenter are aligned on the local mechanical axis (z-axis, for example) of the new coordinate system. The new mechanical axis remains in use for referencing purposes until expressly changed by another decenter. The order in which displacements and tilts are applied to a given surface is specified using different decenter types and these generate different new coordinate systems; those used in this disclosure are explained below. Alpha, beta, and gamma values are presented in degrees. Aspheric surfaces, if any, as labeled as A(i), and the aperture stop is denoted as S. Notations (both in drawings and description) referring to "R", "G", and "B" refer to wavelengths of about 643.85 nm, 546.1 nm, and 479.99 nm. As shown, the diameter of the first lens element (element 1) is smaller than 3 mm, the overall length of the lens 2120-L is about 5.7 mm, the half=LFOV angle is 55 degrees, and the object distance is 10 mm.

be attached to another endoscope, borescope, robot, drone, or other object or person for independent imaging and image recording, using the device or person it is attached to for navigation and positioning; alternatively, it can allow the

TABLE 2.3

| ELEMENT NUMBER | RADIUS OF CURVATURE | | THICKNESS | APERTURE DIAMETER | | MATERIAL |
|---|---|---|---|---|---|---|
| | FRONT | BACK | | FRONT | BACK | |
| OBJ (OBJECT) | 10.0000 | | 0.0000 | | | AIR |
| 1 | 5.0000 CX | 0.9045 CC | 0.3750 | 2.9120 | 1.6769 | E48R Zeon |
| | | | 0.7237 | | | |
| 2 | 1.7954 CX | 0.6479 CC | 0.3750 | 1.4197 | 1.0164 | E48R Zeon |
| | | | 0.2352 | | | |
| 3 | 1.5221 CX | 6.4297 CC | 0.3750 | 1.0052 | 0.9021 | E48R Zeon |
| | | | 0.1803 | | | |
| 4 | 3.0950 CX | −1.0126 CX | 0.5000 | 0.8168 | 0.6569 | E48R Zeon |
| | | | 0.1000 | | | |
| S | | | APERTURE STOP | 0.4732 | | |
| | | | 0.2134 | | | |
| 5 | 5.6616 CX | −0.6051 CX | 0.7500 | 0.6656 | 0.9215 | E48R Zeon |
| 6 | −0.6051 CC | −2.0729 CX | 0.4000 | 0.9215 | 1.2264 | OKP4HT Osaka |
| | IMAGE DISTANCE = | | 1.4324 | | | |
| IMG(IMAGE) | INF | | | 2.0882 | | |

NOTES
Positive radius indicates the center of curvature is to the right
Negative radius indicates the center of curvature is to the left
Dimensions are given in millimeters
Thickness is axial distance to next surface
Image diameter shown a is a paraxial value, it is not a ray traced value
Other glass suppliers can be used if their materials are functionally equivalent to the extent needed by the design;
REFERENCE WAVELENGTH = 525.0 NM
SPECTRAL REGION = 450.0-600.0 NM

| INFINITE CONJUGATES | |
|---|---|
| EFL = | 1.0380 |
| BFL = | 1.3470 |
| FFL = | 0.8918 |
| F/NO = | 4.3311 |
| AT USED CONJUGATES | |
| REDUCTION = | 0.0953 |
| FINITE F/NO = | 4.5000 |
| OBJECT DIST = | 10.0000 |
| TOTAL TRACK = | 15.6601 |
| IMAGE DIST = | 1.4324 |
| OAL = | 4.2277 |
| PARAXIAL | |
| IMAGE HT = | 0.8302 |
| IMAGE DIST = | 1.4459 |
| SEMI-FIELD | |
| ANGLE = | 55.3000 |
| ENTR PUPIL | |
| DIAMETER = | 0.2397 |
| DISTANCE = | 1.3160 |
| EXIT PUPIL | |
| DIAMETER = | 0.5864 |
| DISTANCE = | −1.1927 |

NOTES
FFL is measured from the first surface
BFL is measured from the last surface Auxiliary Considerations for Implementing an MVID According to an Embodiment of the Invention.

Depending on the environment, a given MVID can be further modified to operate in physical/chemical/biological environments, such as heat/cold, water or fluids, presence of corrosive substances and electro-magnetic interference, as well as regulatory requirements.

For example, the MVID can be configured as an independent imaging device, an endoscope or borescope, or can operator to use the imaging from either of both devices. It can be used to capture still or video images in different formats, including: spectral, multi-spectral, hyper-spectral, absorption, grey-scale, inverted color and binary images, as well as infra-red images.

As discussed, a multi-view imaging device (MVID) or system of the invention may include a single image sensor (such as a Charge Coupled Device, or CCD or a Complementary Metal-Oxide-Semiconductor, or CMOS) or multiple sensors or cameras, to capture multiple views of the object space. The MVID includes an embodiment of the optical imaging system (as discussed elsewhere in this application), and corresponding mechanical housing or casing complemented with or without external or internal illumination sources.

The formed images of the FFOV and LFOV can be configured to be separated in space from one another or be contiguous, but the spatial relationship between different fields of view generally remains unchanged when the corresponding images are captured with a single image sensor. Moreover, any radial gaps between spatially-separated images of different fields of view can be compensated for by the forward or backward movements of the imaging system along the optical axis, thereby allowing for a complete, aggregate image to be obtained with discontinuous views.

To differentiate between the images of the object space seen in the FFOV and in the LFOV, a slight radial gap can be introduced and displayed between these images to help inform the viewer of the distinction between the two (example of such radial gap is shown in FIGS. 7A, 7B, for example, as dark annular bands 788). As an option, an embodiment of the imaging device can also be rotated, in operation, about a longitudinal axis and/or its distal tip turned up, down, left or right to point in a different direction to augment views and to see the sides of tunnels or organs at sharp turns or branches (as in a T or Y junction of pipes or branches of airways in the lungs).

Geometry of a given implementation of the lens system can be varied to provide specific angular ranges of viewing angles in different fields of view as required by a particular application. Depending on the specifics of implementation, the forward viewing angle can be ±90° or smaller, and the rear viewing angle from can be from ±90 to +/−180° or smaller. As an example, for imaging of the inner surface of colon, the FFOV can be defined by the viewing angle range of, e.g., ±70°, while the LFOV can be defined within the range of viewing angles of e.g., ±100-150° to successfully inspect colon areas hidden in front of about 100 folds and rectal valves that are not visible with the forward view alone. In contrast, for inspecting the turbine blades of an aircraft engine, a forward view (e.g. ±60°) would be paired with a reverse angle of view of e.g., ±140-180°.

As another example, when inspecting the inner walls of a typical industrial pipe, the forward view range of viewing angles (e.g. ±30°) would be used primarily for navigation of the imaging probe, while a lateral view within the range of ±90-150° would provide the required image from the surface of the pipe to show any cracks, debris, or other structural defects.

In yet another example, the range of forward viewing angles can be chosen to be large for inspecting a room or container through a small opening, or the top or base of the human bladder through the urethra. Such an optical system may be configured to possess a FFOV corresponding to the range of viewing angles of ±60°, and an LFOV corresponding to the range of viewing angles ±150-180°. In both cases, a view in the LFOV will provide concurrent images of people or structures hidden from forward view, or the bladder neck while the simultaneously acquiring a view in the FFOV, without losing either of these views and without a need for rotation of the optical system about its axis and/or a need to turn the tip of the imaging probe. In a related embodiment that may find its use in, e.g., robotic surgery, a substantially 3-dimensional or stereoscopic view of the object space acquired in the FFOV with an imaging probe that contains two optical imaging systems can be combined with a view in an LFOV within the range of viewing angles of, e.g. ±140-180° to allow a clinical specialist (a surgeon, for instance) who is usually located remotely to see instruments and devices that are being introduced to a biological tissue by an assistant, and to insure that small cuts and perforations to the intestines, bladder, blood vessels and nerves are avoided during the instrument entry. The view obtained in the LFOV can be displayed around and surrounding the view representing the FFOV when instruments are being introduced and eliminated (e.g., electronically), thereby allowing the surgeon to concentrate on the forward view alone.

Yet another related embodiment (such as that discussed in reference to FIGS. 20A, 20B, 21, 22, 23A, 23B, 24) could offer the formation of an image in the LFOV only, in isolation, by itself (without including the forward view), within a range of viewing angles of e.g.,)±(90°-150° without a forward view. When an embodiment of the optical system of the invention is used in very small or tights spaces (e.g., in blood vessels, or the bile or pancreatic ducts or the fallopian tubes, or very narrow pipes, such as the surgical channels of endoscopes), it may be useful to provide only the LFOV-related views, where the optical apparatus of the invention can be advanced to the area of interest through a catheter using fluoroscopic guidance. Such an apparatus can also be passed through an endoscope biopsy channel or over the outside of a scope, or through a catheter in a blood vessel or ureter, to provide a rear/oblique view as a separate image to complement the forward view of an endoscope. This may be useful in imaging the surfaces of very narrow pipes in industry or channels of medical endoscopes.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. In one specific case, the terms "approximately", "substantially", and "about", when used in reference to a numerical value, represent a range of plus or minus 20% with respect to the specified value, more preferably plus or minus 10%, even more preferably plus or minus 5%, most preferably plus or minus 2% with respect to the specified value.

The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes. Other specific examples of the meaning of the terms "substantially", "about", and/or "approximately" as applied to different practical situations may have been provided elsewhere in this disclosure.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

In addition, it is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

It is appreciated that the imaging probe of the invention, generally and whether or not such configuration is expressed in the attached drawings, includes a front or distal portion in which an opto-electronic circuitry with an embodiment of the optical system of the invention is/are disposed, a proximal portion preferably removably connected to at least a programmable processor and/or an appropriate display device, as well as the housing or sheath (throughout which the optical and/or electrical members operably connecting the programmable processor with the opto-electronic circuitry.

The operation of embodiments of the invention, therefore, may require the use of a computer-readable processor/controller the operation of which is governed by specifically coded instructions stored in a tangible, non-transitory storage memory. Such processor is specifically-programmed to perform at least the steps of collecting optical data through the optical system of the imaging probe as described, and processing these data to display the images of the object space scene(s) at an appropriately-chosen display device, thereby transforming the acquired optical data into a tangible visually-perceivable by the use representation of the object space. The memory may be random access memory (RAM), read-only memory (ROM), flash memory or any other memory, or combination thereof, suitable for storing control software or other instructions and data. Instruction information may be conveyed to a processor through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components. Accordingly, a computer-program product encoded in a non-transitory tangible computer readable storage medium and useable with a programmable computer processor to generate portions of images and full images discussed in this disclosure from optical information received by the optical detector (with which the processor is operably cooperated) is also within the scope of the invention. Computer-code implementing all above-discussed image-acquisition and image-transformation steps, and the processor programmed with such computer code are within the scope of the invention as well.

Disclosed aspects, or portions of these aspects, may be combined in ways not listed above. Accordingly, the invention should not be viewed as being limited to the disclosed embodiment(s).

What is claimed is:

1. An optical system having an optical axis, a front field of view (FFOV) and a lateral field of view (LFOV), and comprising:
    a front lens,
    a rear lens,
        wherein the front lens is dimensioned to collect only first light from a first portion of an object space that is covered by the FFOV and forward said first light through the rear lens towards an image plane of the optical system,
        wherein a rear lens is dimensioned to collect both the first light from the front lens and second light from a second portion of said object space that is covered by the LFOV and image it onto the image plane; and
    an odd number of reflectors separating the front lens from the rear lens and configured to reflect said second light towards the rear lens, wherein a first reflector from said odd number of optical reflectors is not a ring reflector and has an involute reflective surface with an optical aperture centered at the optical axis,
    wherein the optical system is configured to form an optical image of said object space, the optical image including:
        a first portion of the image having a first perimeter that circumscribes an axial point of the first portion of the image,
        a second portion of the image dimensioned as a stripe or band having a second perimeter and located outside of the first perimeter,
        wherein the first portion of the image represents said first portion of the object space,
        wherein the second portion of the image represents said second portion of the object space,
        and
        wherein a first directionality of the first portion of the image and a second directionality of the second portion of the image are the same.

2. The optical system according to claim 1, wherein one of the following conditions is satisfied:
    i) the optical system comprises a mangin mirror element one surface of which is configured as said involute reflective surface; and
    ii) said first reflector is a stand-alone optical reflector.

3. The optical system according to claim 2, wherein a spatial profile of said involute reflective surface in a plane containing the optical axis is represented by a non-analytic function of a viewing angle of the optical system.

4. The optical system according to claim 1,
wherein a spatial profile of said involute reflective surface in a plane containing the optical axis is represented by a function of a viewing angle of the optical system.

5. The optical system according to claim 4, wherein said function of the viewing angle is not an analytic function.

6. The optical system according to claim 1, further comprising an optical detector disposed at said image plane.

7. An imaging probe containing the optical system of claim 1, further comprising electronic circuitry that is operably cooperated with the image plane to collect an electrical signal representing said optical image and that is configured to generate a visually-perceivable representation of said optical image,
wherein said imaging probe is devoid of a light guide configured to supply electromagnetic radiation towards the FFOV.

8. A method for forming an image of the object space with the use of an optical imaging system that has an optical axis, a front field of view (FFOV), a lateral FOV (LFOV), an optical detector, and programmable electronic circuitry operably cooperated with the optical detector,
the image including:
a first portion of the image having a first perimeter that circumscribes an axial point of the first portion of the image,
a second portion of the image dimensioned as a stripe or band having a second perimeter and located outside of the first perimeter,
wherein the first portion of the image represents a first portion of the object space covered by the FFOV,
wherein the second portion of the optical image represents a second portion of the object space covered by the LFOV,
and wherein a first directionality of the first portion of the image and a second directionality of the second portion of the image are the same,
the method comprising:
forming, with the use of the optical detector, the first portion of the image by collecting first light from the FFOV through both first and second optical elements of said optical system,
wherein the first optical element is an optical element directly exposed to the first portion of the object space, and wherein the second optical element is immediately adjoining the first optical element,
forming, with the use of the optical detector, a third portion of the image by at least in part collecting second light from the LFOV of the optical system through an edge surface of the second element of the optical system while preventing said second light from traversing any surface of the first optical element,
wherein the third portion of the image is dimensioned as said stripe or band having the second perimeter and located outside of the first perimeter, and wherein a third directionality of the third portion of the image is opposite to the second directionality;
transforming irradiance of the third portion of the image to create the second portion of the image by radially redistributing said irradiance of the third portion of the image with respect to a circle of a chosen radius located between inner and outer perimeters of said second portion of the image; and
with the use of said programmable electronic circuitry, generating a report containing a visually-perceivable representation of said image.

9. The method according to claim 8, wherein said preventing includes reflecting the second light at a reflective surface that is congruent with a surface of the second optical element.

10. The method according to claim 9, wherein said surface of the second optical element is an aspheric optical surface.

11. The method according to claim 8, wherein said forming the third portion of the image includes causing said second light to interact with three different surfaces of the second optical element, wherein two of the three different surfaces cross the optical axis and a remaining of the three different surfaces is said edge surface.

12. The method according to claim 8,
wherein said transforming irradiance includes replacing a value of a first irradiance at a first pixel located along a chosen radius of said third portion of the image with a value of a second irradiance at a second pixel located along the chosen radius of said third portion while replacing the value of the second irradiance at the second pixel with the value of the first irradiance at the first pixel, and
wherein locations of the first and second pixels are symmetric with respect to a circle of radius that is defined as a weighted combination of (i) a geometric mean of outer and inner radii of the third portion of the image and (ii) an arithmetic mean of said outer and inner radii.

13. The method according to claim 12, wherein said preventing includes reflecting the second light at a reflective surface that is congruent with a surface of the second optical element.

* * * * *